United States Patent [19]

Giencke et al.

[11] Patent Number: 5,250,530

[45] Date of Patent: Oct. 5, 1993

[54] AMINOPYRIMIDINE DERIVATIVES, AND THEIR USE AS FUNGICIDES

[75] Inventors: Wolfgang Giencke, Hofheim am Taunus; Burkhard Sachse, Kelkheim; Heinrich Wicke, Eppstein/Taunus, all of Fed. Rep. of Germany

[73] Assignee: Hoechst Aktiengesellschaft, Frankfurt am Main, Fed. Rep. of Germany

[21] Appl. No.: 549,764

[22] Filed: Jul. 9, 1990

[30] Foreign Application Priority Data

Jul. 11, 1989 [DE] Fed. Rep. of Germany ....... 3922735

[51] Int. Cl.$^5$ ............... C07D 401/04; C07D 401/14; A01N 43/54
[52] U.S. Cl. ..................... 514/256; 514/212; 514/234.5; 514/235.8; 514/258; 514/269; 514/232.2; 514/232.5; 514/254; 514/253; 514/252; 540/600; 540/601; 544/327; 544/328; 544/298; 544/319; 544/295; 544/253; 544/119; 544/122; 544/123; 544/82; 544/80
[58] Field of Search ............. 544/327, 328, 298, 319, 544/295, 253, 119, 122, 123; 540/600, 601; 514/212, 234.5, 235.8, 258, 269, 256, 232.2, 232.5, 256, 254, 253, 252

[56] References Cited

U.S. PATENT DOCUMENTS 4,109,092  8/1978  Lesher ............................ 544/328

FOREIGN PATENT DOCUMENTS 0234104  9/1987  European Pat. Off. .
0259139  3/1988  European Pat. Off. .
0270362  6/1988  European Pat. Off. .

OTHER PUBLICATIONS

Lafferty et al J. Org. Chem., vol. 32, (1967), S. 1591 ff.
Brown et al (I) Australian Journal of Chemistry, Band 35, No. 6, 1982, pp. 1203–1207.
Brown et al. (II) Australian Journal of Chemistry, Band 33, No. 10, 1980, pp. 2291–2298.

Primary Examiner—John M. Ford
Attorney, Agent, or Firm—Curtis, Morris & Safford

[57] ABSTRACT

Aminopyrimidine derivatives, their preparation, and agents containing them, and their use as fungicides comprising

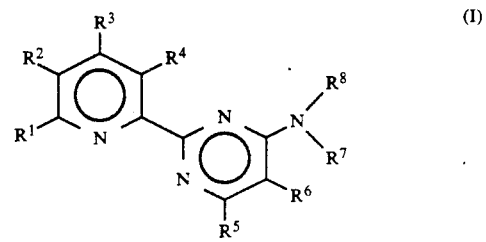

(I)

in which
$R^1$ is alkyl, alkoxyalkyl, alkylthioalkyl, cycloalkyl, alkenyl, alkynyl, cycloalkylalkyl, substituted aminoalkyl, phenyl, phenylalkyl, phenoxyalkyl, phenylmercaptoalkyl or phenoxyphenoxyalkyl, $R^2$, $R^3$ and $R^4$ are H, alkyl, or phenyl, $R^5$ is H, alkyl, cycloalkyl, cycloalkylalkyl, haloalkyl, alkoxy, alkylthio, alkoxyalkyl, $R^7R^8N$-,alkylthioalkyl, $R^7R^8N$-alkyl, halogen, alkenyl, alkynyl, phenyl, phenoxy, phenylalkyl, phenoxyalkyl, phenylmercaptoalkyl, phenylmercapto, phenylalkoxy or phenylalkylthio, R5 is H, alkyl, alkyloxy, alkenyloxy, alkynyloxy, alkylthio, halogen, or phenyl or $R^5$ and $R^6$ together form a chain, and $R^7$ and $R^8$ are H, alkyl, alkoxyalkyl, hydroxyalkyl, alkylthioalkyl, alkenyl, substituted formyl, phenyl or phenylalkyl, or $R^7$ or $R^8$ together with the nitrogen atom form a heterocycle wherein phenyl and cycloalkyl moieties can be substituted, as well as the salts thereof, have advantageous fungicidal properties.

8 Claims, No Drawings

AMINOPYRIMIDINE DERIVATIVES, AND THEIR USE AS FUNGICIDES

DESCRIPTION

The present invention relates to novel aminopyrimidine derivatives, to processes for their preparation to agents containing them, and to their use as fungicides.

Pyrimidine derivatives have already been disclosed as effective components in fungicidal agents (cf. EP-A-270,362, EP-A-259,139, EP-A 234,104). However, the action of these pyrimidine derivatives is not always satisfactory, in particular when low amounts are applied.

Novel pyrimidine derivatives which have advantageous actions in the control of a broad range of phytopathogenic fungi, in particular at low application rates, have been found.

The present invention therefore relates to the compounds of the formula I where

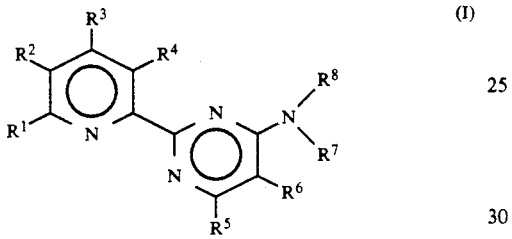

$R^1$ is hydrogen, $(C_1-C_6)$alkyl, $(C_1-C_4)$alkoxy-$(C_1-C_4)$alkyl, $(C_1-C_4)$ alkylthio- $(C_1-C_4)$alkyl, $(C_2-C_6)$alkenyl, $(C_2-C_6)$alkynyl, $(C_3-C_7)$Cycloalkyl and $(C_3-C_7)$cycloalkyl-$(C_1-C_4)$alkyl, where the last two radicals can be up to trisubstituted in the cycloalkyl moiety by $(C_1-C_4)$alkyl, or is a group $R^7R^8N$-$(C_1-C_4)$alkyl, phenyl, phenoxy-$(C_1-C_4)$alkyl, phenylmercapto-$(C_1-C_4)$-alkyl, phenyl-$(C_1-C_4)$alkyl and phenoxyphenoxy$(C_1-C_4)$ alkyl, where the last five radicals can be up to trisubstituted in the phenyl moiety by halogen, nitro, cyano, $(C_1-C_4)$ alkyl, $(C_1-C_4)$ alkoxy, $(C_1-C_4)$alkylthio, $(C_1-C_4)$haloalkyl or $(C_1-C_4)$haloalkoxy, $R^2$, $R^3$ and $R^4$ independently of one another are hydrogen, $(C_1-C_6)$alkyl or phenyl, where the phenyl radical can be up to trisubstituted by halogen, nitro, cyano, $(C_1-C_4)$alkyl, $(C_1-C_4)$alkoxy, $(C_1-C_4)$alkylthio, $(C_1-C_4)$haloalkyl or $(C_1-C_4)$haloalkoxy, $R^5$ is hydrogen, $(C_1-C_6)$alkyl, $(C_3-C_7)$cycloalkyl or $(C_3-C_7)$cycloalkyl-$(C_1-C_4)$alkyl, where the last two radicals can be up to trisubstituted in the cycloalkyl moiety by $(C_1-C_4)$alkyl, or is $(C_1-C_4)$haloalkyl, $(C_1-C_4)$alkoxy, $(C_1-C_4)$alkylthio $(C_1-C_4)$alkoxy$(C_1-C_4)$alkyl, a group $R^7R^8N$-, $(C_1-C_4)$alkylthio$(C_1-C_4)$alkyl, a group $R^7R^8N$-$(C_1-C_4)$alkyl, halogen, $(C_2-C_6)$alkenyl, $(C_2-C_6)$alkynyl, phenyl, phenoxy, phenyl $(C_1-C_4)$alkyl, phenoxy-$(C_1-C_4)$alkyl, phenylmercapto-$(C_1-C_4)$alkyl, phenylmercapto, phenyl$(C_1-C_4)$alkoxy or phenyl-$(C_1-C_4)$alkylthio, where the last eight radicals can be up to trisubstituted in the phenyl moiety by halogen, nitro, cyano, $(C_1-C_4)$alkyl, $(C_1-C_4)$alkoxy, $(C_1-C_4)$alkylthio,$(C_1-C_4)$haloalkyl or $(C_1-C_4)$haloalkoxy;

$R^6$ is hydrogen, $(C_1-C_4)$alkyl, $(C_1-C_4)$alkoxy, $(C_2-C_6)$alkenyloxy, $(C_2-C_6)$alkynyloxy, $(C_1-C_4)$alkylthio, halogen or phenyl, where the phenyl radical can be up to trisubstituted by halogen, nitro, cyano, $(C_1-C_4)$alkyl, $(C_1-C_4)$alkoxy, $(C_1-C_4)$alkylthio, $(C_1-C_4)$haloalkyl or $(C_1-C_4)$haloalkoxy, or $R^5$ and $R^6$ together form a polymethylene chain of the formula —$(CH_2)_m$— with m being 3-4 and $R^7$ and $R^8$ independently of one another are hydrogen, $(C_1-C_6)$alkyl, $(C_1-C_4)$alkoxy-$(C_1-C_6)$alkyl, hydroxy$(C_1-C_6)$alkyl, $(C_1-C_4)$alkylthio-$(C_1-C_6)$alkyl, $R^9R^{10}N(C_1-C_6)$alkyl, $(C_3-C_6)$alkenyl, $(C_3-C_6)$alkynyl, $(C_3-C_7)$cycloalkyl or $(C_3-C_7)$cycloalkyl-$(C_1-C_4)$alkyl, where the last two radicals can be up to trisubstituted in the cycloalkyl moiety by $(C_1-C_4)$alkyl; or are formyl, phenyl or phenyl-$(C_1-C_4)$alkyl, where the last two radicals can be up to trisubstituted in the phenyl moiety by halogen, nitro, cyano, $(C_1-C_4)$alkyl, $(C_1-C_4)$alkoxy, $(C_1-C_4)$alkylthio, $(C_1-C_4)$haloalkyl or $(C_1-C_4)$haloalkoxy;

or the two radicals $R^7$ and $R^8$ together with the nitrogen atom to which they are bonded stand for an unsubstituted or up to tetrasubstituted 5- to 7-membered, saturated or unsaturated heterocycle which has 1 to 3 identical or different hetero atoms, preferably the hetero atoms nitrogen, oxygen and/or sulfur, and the substituent $(C_1-C_4)$alkyl;

$R^9$ and $R^{10}$ independently of one another are hydrogen, $(C_1-C_6)$alkenyl, $(C_3-C_6)$alkenyl, $(C_3-C_6)$alkynyl, $(C_3-C_7)$cycloalkyl or $(C_3-C_7)$cycloalkyl-$(C_1-C_4)$alkyl, where the last two radicals can be up to trisubstituted in the cycloalkyl moiety by $(C_1-C_4)$alkyl; or are formyl, phenyl, phenyl$(C_1-C_4)$alkyl, where the last two radicals can be up to trisubstituted in the phenyl moiety by halogen, nitro, cyano, $(C_1-C_4)$alkyl, $(C_1-C_4)$alkoxy, $(C_1-C_4)$alkylthio, $(C_1-C_4)$haloalkyl or $(C_1-C_4)$haloalkoxy;

or the two radicals $R^9$ and $R^{10}$ together with the nitrogen atom to which they are bonded stand for an unsubstituted or up to tetrasubstituted 5- to 7-membered, saturated or unsaturated heterocycle which has 1 to 3 identical or different hetero atoms, preferably the hetero atoms nitrogen, oxygen and/or sulfur and the substituent $(C_1-C_4)$alkyl; and the acid addition salts thereof.

In this context, the alkyl, alkenyl or alkynyl radicals can be straight-chain or branched. Halogen is F, Cl, Br or I, preferably P, Cl and Br. Here and below the prefix "halo" in the name of a substituent means that this substituent can occur once or several times in an identical or different meaning. The prefix "halo" embraces fluorine, chlorine, bromine or iodine, in particular fluorine, chlorine or bromine. Examples of haloalkyl which may be mentioned are: $CF_3$, $CF_2CHF_2$, $CF_2CF_3$, $CCl_3$, $CCl_2F$, $CF_2CF_2CF_3$, $CF_2CHFCF_3$ and $(CF_2)_3CF_3$. Examples of haloalkoxy are $OCF_3$, $OCF_2CHF_2$ or $OCF_2CF_2CF_3$.

Preferred amongst the compounds of the formula I are those in which $R^1$ is hydrogen, $(C_1-C_6)$alkyl, phenyl, phenyl-$(C_1-C_2)$alkyl, phenoxyphenoxy-$(C_1-C_2)$alkyl or phenoxy- $(C_1-C_2)$alkyl, where the last f our radicals can be up to trisubstituted in the phenyl moiety by halogen or $(C_1-C_4)$alkyl; or is $(C_1-C_3)$alkoxy-$(C_1-C_2)$alkyl, $R^2$ and $R^3$ independently of one another are hydrogen, $(C_1-C_3)$alkyl or phenyl, where the phenyl radical can be up to trisubstituted by halogen or $(C_1-C_4)$alkyl, $R^4$ is hydrogen, $R^5$ is hydrogen, $(C_1-C_6)$alkyl, $(C_3-C_6)$cycloalkyl, $(C_5-C_6)$cycloalkyl-$(C_1-C_3)$alkyl, halogen, phenyl or phenyl$(C_1-C_2)$alkyl, where the last two radicals can be unsubstituted or up to trisubstituted in the phenyl moiety by halogen, $(C_1-C_4)$alkyl or $(C_1-C_4)$alkoxy, $R^6$ is hydrogen, $(C_1-C_4)$alkyl, halogen, phenyl or $(C_1-C_3)$alkoxy, or $R^5$ and $R^6$ together form a polymethylene chain of the formula $-(CH_2)_m-$ with m being 3-4, and $R^7$ and $R^8$ independently of one another are hydrogen, $(C_1-C_6)$alkyl, $(C_1-C_4)$alkoxy-$(C_1-C_6)$-alkyl, hydroxy$(C_1-C_6)$alkyl, $(C_1-C_4)$alkylthio-$(C_1-C_6)$alkyl, $R^9R^{10}N(C_1-C_4)$alkyl, $(C_3-C_4)$alkenyl, $(C_3-C_4)$alkynyl, $(C_3-C_6)$cycloalkyl or $(C_3-C_6)$cycloalkyl-$(C_1-C_3)$alkyl, where the last two radicals can be up to disubstituted in the cycloalkyl moiety by $(C_1-C_2)$alkyl; or are formyl, phenyl or phenyl-$(C_1-C_2)$alkyl, where the last two radicals can be up to disubstituted in the phenyl moiety by halogen, $(C_1-C_3)$alkyl, $(C_1-C_3)$alkoxy, trifluoromethyl or trichloromethyl;

or the two radicals $R^7$ and $R^8$ together with the nitrogen atom to which they are bonded stand for an unsubstituted or up to disubstituted 5- to 7-membered, saturated or unsaturated heterocycle which has 1 or 2 identical or different hetero atoms, preferably the hetero atoms nitrogen and/or oxygen, and the substituent $(C_1-C_3)$alkyl, $R^9$ and $R^{10}$ independently of one another are hydrogen, $(C_1-C_6)$alkyl, $(C_3-C_6)$alkenyl, $(C_3-C_6)$alkynyl $(C_3-C_7)$cycloalkyl or $(C_3-C_7)$cycloalkyl-$(C_1-C_4)$alkyl, where the last two radicals can be up to trisubstituted in the cycloalkyl moiety by $(C_1-C_4)$alkyl; or are formyl, phenyl or phenyl $(C_1-C_4)$alkyl, where the last two radicals can be up to trisubstituted in the phenyl moiety by halogen, nitro, cyano, $(C_1-C_4)$alkyl, $(C_1-C_4)$alkoxy, $(C_1-C_4)$alkylthio, $(C_1-C_4)$haloalkyl or $(C_1-C_4)$haloalkoxy;

or the two radicals $R^9$ and $R^{10}$ together with the nitrogen atom to which they are bonded represent an unsubstituted or up to tetrasubstituted 5- to 7-membered, saturated or unsaturated heterocycle which has 1 to 3 identical or different hetero atoms, preferably the hetero atoms nitrogen, oxygen and/or sulfur and the substituent $(C_1-C_4)$alkyl; and the acid addition salts thereof.

The following acids are suitable for the preparation of the acid addition salts of the compounds of the formula I: hydrohalic acids, such as hydrochloric acid or hydrobromic acid, furthermore phosphoric acid, nitric acid, sulfuric acid, monofunctional or bifunctional carboxylic acids and hydroxycarboxylic acids, such as acetic acid, maleic acid, succinic acid, fumaric acid, tartaric acid, citric acid, salicylic acid, sorbic acid or lactic acid, and also sulfonic acids, such as p-toluenesulfonic acid or 1,5-naphthalenedisulfonic acid. The acid addition salts of the compounds of the formula I can be obtained in a simple manner by customary salt formation methods, for example by dissolving a compound of the formula I in a suitable organic solvent and adding the acid, and they can be isolated in a known manner, for example by filtration, and, if appropriate, purified by washing with an inert organic solvent.

The present invention also relates to a process for the preparation of the compounds of the formula I, wherein a compound of the formula II is reacted with a compound of the formula III in the presence of a base.

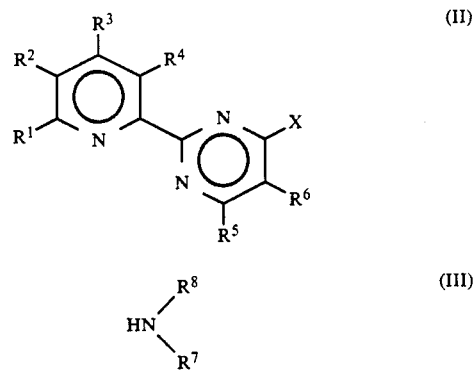

In this context, the substituents $R^1$ to $R^8$ are as defined in formula I. X stands for halogen. Halogen is fluorine, chlorine, bromine or iodine, in particular chlorine or bromine.

The compounds II are preferably reacted with III in inert aprotic solvents such as, for example, acetonitrile, dichloromethane, toluene, xylene, tetrahydrofuran, dioxane, dialkyl ethers, such as diethylene glycol dialkyl ethers, in particular diethylene glycol diethyl ether, or DMF, at temperatures between $-10°$ C. and the boiling point of the solvent. Bases which are suitable are those which are customary for this type of reaction, such as, for example, carbonates and hydrogen carbonates of alkali metals and alkaline earth metals, alkali metal hydroxides, alkali metal alcoholates such as potassium tert.-butylate, or tertiary amines, pyridine or substituted pyridine bases (for example 4-dimethylaminopyridine).

It is also possible for a second equivalent of the compounds of the general formula III to take over the base function.

The compounds of the formula II can be prepared by known processes (cf. EP-A-234,104, EP-A-259,139, EP-A-270,362, J. Org. Chem. 12, 1591, (1967)). The compounds of the formula III are known and readily accessible (Houben-Weyl, Methoden der Org. Chemie [Methods in Organic Chemistry], Vol. XI/1).

The compounds of the formula I according to the invention are distinguished by an excellent fungicidal action. Fungal pathogens which have already penetrated the plant tissue can be successfully controlled curatively. This is particularly important and advantageous in the case of those fungal diseases where control with other customary fungicides after infection has taken place is no longer effective. The range of action of the claimed compounds embraces a multitude of various economically important phytopathogenic fungi such as, for example, Pyricularia oryzae, Venturis inaequalis, Cercospora beticola, powdery mildew species, Fusarium species, Plasmopora viticola, Pseudoperonospora cubensis, various rusts and Pseudocercosporelia herpotrichoides. It acts particularly well on Botrytis cinerea strains which are sensitive and resistant to benzimidazol and dicarboximide.

In addition, the compounds according to the invention are also suitable for use in industrial sectors, for example as wood protection agents, as preservatives in paints, in cooling lubricants for metal processing, or as preservatives in drilling and cutting oils.

The invention also relates to agents which contain the compounds of the formula I besides suitable formulation auxiliaries.

The agents according to the invention contain the active substances of the formula I in general in amounts of from 1 to 95% by weight.

They can be formulated in many ways, depending on the biological and/or physicochemical parameters. The following formulations are therefore possible: wettable powders (WP), emulsifiable concentrates (EC), aqueous solutions (SC), emulsions, sprayable solutions, oil- or water-based dispersions (SC), suspoemulsions (SC), dusts (DP), seed treatment agents, granules in the form of microgranules, spray granules, coated granules and adsorption granules, water-dispersible granules (WG), ULV formulations, microcapsules, waxes or baits.

These individual formulation types are known in principle and are described, for example, in: Winnacker-Küchler, Chemische Technologie [Chemical Technology], Volume 7, C. Hauser Verlag Munich, 4th Ed., 1986; van Valkenburg, "Pesticides Formulations", Marcel Dekker N.Y., 2nd Ed. 1972-73; K Martesn, "Spray Drying Handbook", 3rd Ed. 1979, G. Goodwin Ltd. London.

The formulation auxiliaries required, such as inert materials, surfactants, solvents and other additives, are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; Marschen, "Solvents Guide", 2nd Ed., Interscience, N.Y. 1950; McCutcheon's "Detergents and Emulsifiers Annual", MC Publ. Corp. Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts]", Wiss. Verlags-gesell., Stuttgart 1976; Winnacker-Küchler, "Chemische Technologie [Chemical Technology]", Volume 7, C. Hauser Verlag Munich, 4th Ed. 1986.

Combinations with other pesticidally active substances, fertilizers and/or growth regulators may also be prepared on the basis of these formulations, for example in the form of a readymix or as a tank mix.

Wettable powders are preparations which are uniformly dispersible in water and which, besides the active substance, also contain wetting agents, for example polyoxethylated alkylphenols, polyoxethylated fatty alcohols, alkylsulfonates or alkylphenolsulfonates, and dispersing agents, for example sodium ligninsulfonate, sodium 2,2'-dinaphthylmethane-6,6'-disulfonate, sodium dibutylnaphthalenesulfonate, or alternatively sodium oleylmethyltaurinate, in addition to a diluent or inert substance. Emulsifiable concentrates are prepared by dissolving the active substance in an organic solvent, for example butanol, cyclohexanone, dimethylformamide, xylene and also higher-boiling aromatic compounds or hydrocarbons, with the addition of one or more emulsifiers. Examples of emulsifiers which can be used are: calcium salts of an alkylarylsulfonic acid, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide sorbitan fatty acid esters, polyoxyethylene sorbitan fatty acid esters or polyoxyethylene sorbitol esters.

Dusting agents can be obtained by grinding the active substance with finely divided solid substances, for example talc or natural clays, such as kaolin, bentonite, pyrophyllite or diatomaceous earth. Granules can be produced either by spraying the active substance onto adsorptive, granulated inert material or by applying active substance concentrates onto the surface of carriers, such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

The concentration of active substance in wettable powders is, for example, about 10 to 90% by weight, the remainder to 100% by weight is composed of conventional formulation components. In the case of emulsifiable concentrates, the concentration of active substance can be about 5 to 80% by weight. Formulations in the form of dusts usually contain 5 to 20% by weight of active substance, sprayable solutions about 2 to 20% by weight. In the case of granules, the active substance content depends partly on whether the active compound is liquid or solid and on which granulation auxiliaries, fillers etc. are used.

In addition, the active substance formulations mentioned contain, if appropriate, the adhesives, wetting agents, dispersing agents, emulsifiers, penetrants, solvents, fillers or carriers which are conventional in each case.

For use, the concentrates, present in commercially available form, are diluted, if appropriate, in a customary manner, for example using water in the case of wettable powders, emulsifiable concentrates, dispersions and in some cases, also in the case of microgranules. Preparations in the form of dusts or granulated preparations and also sprayable solutions are usually not further diluted with other inert substances before use.

The application rate required varies with the external conditions, such as, inter alia, temperature and humidity. It can vary within wide limits, for example between 0.005 and 10.0 kg/ha or more of active ingredient; preferably, however, it is between 0.01 and 5 kg/ha.

The active substances according to the invention can be used, in their commercially available formulations, either by themselves or in combination with other fungicides known from the literature.

Examples of fungicides which are known from the literature and which can be combined according to the invention with the compounds of the formula I, are the following products: Imazalil, prochloraz, fenapanil, SSF 105, triflumizol, PP 969, flutriafol, BAY-MEB 6401, propiconazol, etaconazol, diclobutrazol, bitertanol, triadimefon, triadimenol, fluotrimazol, tridemorph, dodemorph, fenpropimorph, falimorph, S-32165, chlobenzthiazone, parinol, buthiobate, fenpropidin, triforine, fenarimol, nuarimol, triarimol, ethirimol, dimethirimol, bupirimate, rabenzazole, tricyclazole, fluobenzimine, pyroxyfur, NK-483, PP-389, pyroquilon, hymexazole, fenitropan, UHF-8227, cymoxanil, dichlorunanid, captafol, captan, folpet, tolylfluanid, chlorothalonil, etridiazol, iprodione (formula II), procymidon, vinclozolin, metomeclan, myclozolin, dichlozolinate, fluorimide, drazoxolan, chinomethionate, nitrothalisopropyl, dithianon, dinocap, binapacryl, fentin acetate, fentin hydroxide, carboxin, oxycarboxin, pyracarbolid, methfuroxam, fenfuram, furmecyclox, benodanil, mebenil, mepronil, flutalanil, fuberidazole, thiabendazole, carbendazim, benomyl, thiophanate, thiophanatemethyl, CGD-94340 F, IKF-1216, mancozeb, maneb, zineb, nabam, thiram, probineb, prothiocarb, propamocarb, dodine, guazatine, dicloran, quintozene, chloroneb, tecnazene, biphenyl, anilazine, 2-phenylphenol, copper compounds such as Cu oxychloride, oxine-Cu, Cu oxides, sulfur and fosetyl aluminum, sodium dodecylbenzenesulfonate, sodium dodecylsulfate, sodium $C_{13}/C15$-alcohol ether sulfonate, sodium cetostearyl phosphate ester, dioctyl sodium sulfosuccinate, sodium isopropylnaphthalenesulfonate, sodium methylenebisnaphthalenesulfonate, cetyl trimethylammonium chloride, salts of long-chain primary, secondary or tertiary amines, alkylpropyleneamines, laurylpyridinium bromide, ethoxylated quaternized fatty amines, alkyldimethylbenzylammonium chloride and 1-hydroxyethyl-2-alkylimidazoline.

The abovementioned combination components represent known active substances, most of which are described in CH. R. Worthing, U. S. B. Walker, The Pesticide Manual, 7th Ed. (1983), British Crop Protection Council.

Moreover, the active substances according to the invention, in particular those of the examples mentioned, can be present in their commercially available formulations and in the use forms prepared from these formulations in a mixture with other active substances, such as insecticides, attractants, sterilants, acaricides, nematicides, fungicides, growth-regulating substances or herbicides. Examples of insecticides include, inter alia, phosphoric esters, carbamates, carboxylic esters, formamidines, tin compounds and substances prepared by microorganisms. Preferred mixture components are:

1. from the group of the phosphoric esters azinphosethyl, azinphos-methyl, 1-(4-chlorophenyl-4-(O-ethyl, S-propyl)phosphoryloxypyrazole (TIA 230), chlorpyrifos, coumaphos, demeton, demeton-S-methyl, diazinon, dichlorvos, dimethoate, ethoprophoo, etrimfos, fenitrothion, fenthion, heptenophoo, parathion, parathion-methyl, phosalone, pirimiphos-ethyl, pirimiphos-methyl, profenofos, prothiofos, sulprofos, triazophos and trichlorphon.

2. from the group of the carbamates aldicarb, bendiocarb, BPMC (2-(1-methylpropyl)phenylmethylcarbamate), butocarboxim, butoxicarboxim, carbaryl, carbofuran, carbosulfan, cloethocarb, isoprocarb, methomyl, oxamyl, pirimicarb, promecarb, propoxur and thiodicarb.

3. from the group of the carboxylic esters allethrin, alphamethrin, bioallethrin, bioresmethrin, cycloprothrin, cyfluthrin, cyhalothrin, cypermethrin, deltamethrin, alpha-cyano-3-phenyl-2-methylbenzyl 2,2-dimethyl-3-(2-chloro-2-trifluoromethylvinyl)-cyclopropanecarboxylate (FMC 54800), fenpropathrin, fenfluthrin, fenvalerate, flucythrinate, flumethrin, fluvalinate, permethrin, resmethrin, tralomethrin.

4. from the group of the formamidines amitraz and chlordimeform 5. from the group of the tin compounds azocyclotin, cyhexatin and fenbutatin oxide 6. others abamectin, Bacillus thuringiensis, benoultap, binapacryl, bromopropylate, buprofecin, camphechlor, cartap, chlorbenzilate, chlorfluazuron, 2-(4-chlorophenyl)-4,5-diphenylthiophene (UBI-T 930), chlofentezine, 2-naphthylmethyl cyclopropanecarboxylate (Ro 12-0470), cyromacin, DDT, dicofol, N-(3,5-dichloro-4-(1,1,2,2-tetrafluoroethoxy)phenylamino)carbonyl)- 2,6-difluorobenzamide (XRD 473), diflubenzuron, N-(2,3-dihydro-3-methyl-1,3-thiazol-2-ylidene)2,4-xylidine, dinobuton, dinocap, endosulfan, fenoxycarb, fenthiocarb, flubenzimine, flufenoxuron, gamma-HCH, hexythiazox, hydramethylnon (AC 217 300), ivermectin, 2-nitromethyl-4,5dihydro-6H-thiazine (SD 52618), 2-nitromethyl-3,4-dihydrothiazole (SD 35651), 2-nitromethylene-1,3-thiazinan-3-ylcarbamaldehyde (WL 108 477), propargite, teflubenzuron, tetradifon, tetrasul, thiocyclam, triflumaron, and nuclear polyhedrosis and granulosis viruses.

The active substance content of the use forms prepared from the commercially available formulations can vary within broad ranges. The active substance concentration of the use forms can be from 0.0001 to 100% by weight of active substance, preferably between 0.001 and 1% by weight. Application is effected in a conventional fashion, matched to the use forms.

The following examples serve to illustrate the invention.

A. FORMULATION EXAMPLES a) A dust is obtained by mixing 10 parts by weight of active substance and 90 parts by weight of talc as inert material and comminuting the mixture in a hammer mill.

b) A wettable powder which is readily dispersible in water is obtained by mixing 25 parts by weight of active substance, 65 parts by weight of kaolin-containing quartz as inert material, 10 parts by weight of potassium ligninsulfonate and 1 part by weight of sodium oleoylmethyltaurinate as wetting and dispersing agent, and grinding the mixture in a pin disk mill.

c) A dispersion concentrate which is readily dispersible in water is prepared by mixing 40 parts by weight of active substance with 7 parts by weight of a sulfosuccinic monoester, 2 parts by weight of a sodium salt of ligninsulfonic acid and 51 parts by weight of water and grinding the mixture in a ball mill to a fineness of below 5 microns.

d) An emulsifiable concentrate can be prepared from 15 parts by weight of active substance, 75 parts by weight of cyclohexanone as solvent and 10 parts by weight of oxethylated nonylphenol (10 EO) as emulsifier.

e) Granules can be prepared from 2 to 15 parts by weight of active substance and an inert carrier material for granules such as attapulgite, granulated pumice and/or quartz sand. It is advantageous to use a suspension of the wettable powder f rom Example b) with a solids content of 30% which is sprayed onto the surface of attapulgite granules, and these are dried and intimately mixed. The proportion by weight of the wettable powder is about 5% here, and that of the inert carrier material about 95% of the finished granules.

B. CHEMICAL EXAMPLES
4-Methyl-2-(2-methyl-pyridin-6-yl)-6-propylaninopyrinlidine (Example No. 1.2)

To a solution of 1.10 g (5 mmol) of 4-chloro-6-methyl-2-(2-methyl-pyridin-6-yl)-pyrimidine in 30 ml of acetonitrile there are added in succession 0.32 g (5.5 mmol) of propylamine, 0.83 g (6 mmol) of $K_2CO_3$ and 10 mg of benzyltriethylammonium chloride. The reaction mixture is refluxed for 7 hours. After this, all insoluble constituents are f altered off with suction. The filtrate is concentrated, the residue is dissolved in methylene chloride, and the solution is subsequently washed with water, dried over Na₂SO₄ and evaporated in vacuo. 1.15 g (95%) of the title compound are obtained as a yellowish oil.

4-Chloro-6-diethylazino-2-(2-methyl-pyridin-6-yl)pyrinlidine (Example No. 9.5)

To a solution of 1.44 g (6 mmol) of 4.6-dichloro-2-(2-methyl-pyridin-6-yl)-pyrimidin in 30 ml of acetonitrile there are added in succession 0.48 g (6.6 nmol) of diethylamine, 0. 97 g (7.0 mmol) of K₂CO₃ and 10 mg of benzyltriethylammonium chloride. The reaction mixture is stirred for 3 hours at room temperature. After this, all insoluble constituents are filtered of f with suction. The filtrate is concentrated, the residue is dissolved in methylene chloride, and the solution is washed with water, dried over Na₂SO₄ and evaporated in vacuo. 1.73 g (92%) of the title compound are obtained as a greenish oil.

4-Phenyl-6-propylazino-2-(2-methylpyridin-6-yl)pyrimidine hydrochloride (Example No. 200.1)

HCl gas is passed over a period of 1 hour into a solution of 3.4 g (0.01 mol) of 4-phenyl-6-propylamino-2-(2-methylpyridin-6-yl)-pyrimidine. The solid which has precipitated is filtered off with suction. It deliquesces immediately to give a syrupy material.

The compounds of Tables A and B can be prepared in analogy to these examples.

| Abbreviations: | Et = ethyl |
| | Me = methyl |
| | Pr = propyl |

TABLE A (I)

| No. | R¹ | R² | R³ | R⁴ | R⁵ | R⁶ | NR⁷R⁸ | Physical properties |
|---|---|---|---|---|---|---|---|---|
| 1.1 | CH₃ | H | H | H | CH₃ | H | NEt₂ | ¹H-NMR (CDCl₃): d 8.16 t 7.66 d 7.20 s 6.21 q 3.57 s 2.69 d 2.48 t 1.19 [ppm] |
| 1.2 | CH₃ | H | H | H | CH₃ | H | NH propyl | ¹H-NMR (CDCl₃): d 8.19 t 7.70 d 7.19 s 6.22 q 3.26 s 2.67 s 2.45 dq 1.57 t 0.99 [ppm] |
| 1.3 | CH₃ | H | H | H | CH₃ | H | NMe₂ | ¹H-NMR (CDCl₃): d 8.17 t 7.54 d 7.22 s 3.16 s 2.69 s 2.49 [ppm] |
| 1.4 | CH₃ | H | H | H | CH₃ | H | NCH₃C₆H₅ | |
| 1.5 | CH₃ | H | H | H | CH₃ | H | NHMe | |
| 1.6 | CH₃ | H | H | H | CH₃ | H | NHEt | |
| 1.7 | CH₃ | H | H | H | CH₃ | H | (piperidinyl) | |
| 1.8 | CH₃ | H | H | H | CH₃ | H | NHC₆H₅ | |
| 1.9 | CH₃ | H | H | H | CH₃ | H | NCH₂C₆H₅ | |
| 1.10 | CH₃ | H | H | H | CH₃ | H | NHC₆H₄-4-Cl | |
| 2.1 | CH₃ | H | H | H | C₃H₇ | H | NEt₂ | ¹H-NMR (CDCl₃): d 8.14 t 7.65 d 7.19 s 6.22 q 3.69 m 2.69 s 2.65 dq 1.79 t 1.21 t 1.03 [ppm] |
| 2.2 | CH₃ | H | H | H | C₃H₇ | H | NH propyl | ¹H-NMR (CDCl₃): d 8.17 t 7.66 d 7.16 s 6.17 q 3.25 m 2.69 s 2.64 m 1.68 t 1.00 t 0.98 [ppm] |
| 2.3 | CH₃ | H | H | H | C₃H₇ | H | (piperidinyl) | ¹H-NMR (CDCl₃): d 8.14 t 7.66 d 7.20 s 6.34 m 3.70 m 2.80 s 2.75 m 1.64 t 0.98 [ppm] |
| 2.4 | CH₃ | H | H | H | C₃H₇ | H | (pyrrolidinyl) | ¹H-NMR (CDCl₃): d 8.15 t 7.65 t 7.19 s 6.11 m 3.56 t 2.72 s 2.69 m 2.00 m 1.74 t 1.0 [ppm] |

-continued

| No. | | | | | | | | NMR/m.p. |
|---|---|---|---|---|---|---|---|---|
| 2.5 | CH₃ | H | H | H | C₃H₇ | H | 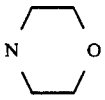 (N-morpholine) | ¹H-NMR (CDCl₃): d 8.16 t 7.68 d 7.20 s 6.84 m 3.77 m 2.75 s 2.66 m 1.78 t 0.99 [ppm] |
| 2.6 | CH₃ | H | H | H | C₃H₇ | H | NMe₂ | ¹H-NMR (DMSO-d₆): 8.07 t 7.68 d 7.29 s 6.52 s 3.11 t 2.59 s 2.54 m 1.79 t 0.95 [ppm] |
| 2.7 | CH₃ | H | H | H | C₃H₇ | H | NHMe | ¹H-NMR (CDCl₃): d 8.16 t 7.67 d 7.16 s 6.19 m 5.41 d 2.94 t 2.66 s 2.63 m 1.79 t 0.97 [ppm] |
| 2.8 | CH₃ | H | H | H | C₃H₇ | H | NCH₃C₆H₅ | m.p.: 145° C. |
| 2.9 | CH₃ | H | H | H | C₃H₇ | H | NHEt | m.p.: 100–102° C. |
| 2.10 | CH₃ | H | H | H | C₃H₇ | H | NHCH₂C≡CH | |
| 2.11 | CH₃ | H | H | H | C₃H₇ | H | NHCH₂—CH=CH₂ | m.p.: 111–113° C. |
| 2.12 | CH₃ | H | H | H | C₃H₇ | H | NH heptyl | |
| 2.13 | CH₃ | H | H | H | C₃H₇ | H | NH butyl | m.p.: 99° C. |
| 2.14 | CH₃ | H | H | H | C₃H₇ | H | NH iso-butyl | m.p.: 119° C. |
| 2.15 | CH₃ | H | H | H | C₃H₇ | H | NH sec-butyl | m.p.: 107° C. |
| 2.16 | CH₃ | H | H | H | C₃H₇ | H | NH pentyl | m.p.: 76° C. |
| 2.17 | CH₃ | H | H | H | C₃H₇ | H | NH benzyl | ¹-NMR (CDCl₃): d 8.19 t 7.67 m 7.36–7.21 d 7.16 s 6.16 t 5.63 d 4.55 t 2.69 s 2.67 dq 1.75 t 0.98 [ppm] |
| 2.18 | CH₃ | H | H | H | C₃H₇ | H | NMe benzyl | ¹H-NMR (CDCl₃): d 8.13 t 7.62 s 7.27 d 7.15 s 6.30 s 4.88 s 3.11 t 2.72 s 2.69 dq 1.77 t 0.98 [ppm] |
| 2.19 | CH₃ | H | H | H | C₃H₇ | H | NH iso-propyl | m.p.: 118–120° C. |
| 2.20 | CH₃ | H | H | H | C₃H₇ | H | NH cyclohexyl | m.p.: 90–92° C. |
| 2.21 | CH₃ | H | H | H | C₃H₇ | H | NH cyclopentyl | m.p.: 146° C. |
| 2.22 | CH₃ | H | H | H | C₃H₇ | H | NHC₆H₅ | |
| 2.23 | CH₃ | H | H | H | C₃H₇ | H | NH (4-Cl—C₆H₄) | m.p.: 103–105° C. |
| 2.24 | CH₃ | H | H | H | C₃H₇ | H | NH (2,4 Cl₂—C₆H₃) | |
| 2.25 | CH₃ | H | H | H | C₃H₇ | H | NH (4-CH₃—C₆H₄) | |
| 2.26 | CH₃ | H | H | H | C₃H₇ | H | NH (4-NO₂—C₆H₄) | |
| 2.27 | CH₃ | H | H | H | C₃H₇ | H | NH (3-CH₃—C₆H₄) | |
| 2.28 | CH₃ | H | H | H | C₃H₇ | H | NH-cyclopropyl | |
| 2.29 | CH₃ | H | H | H | C₃H₇ | H | NH—CH₂CH=C(Me)₂ | |
| 2.30 | CH₃ | H | H | H | C₃H₇ | H | NH—C₆H₄-4-OMe | |
| 2.31 | CH₃ | H | H | H | C₃H₇ | H | NH—C₆H₄-3CF₃ | |
| 2.32 | CH₃ | H | H | H | CH(CH₃)₂ | H | NEt₂ | |
| 2.33 | CH₃ | H | H | H | C₃H₇ | H |  (2,6-dimethylmorpholine) | m.p.: 151° C. |
| 2.34 | CH₃ | H | H | H | CH(CH₃)₂ | H | NH-propyl | m.p.: 105° C. |
| 2.35 | CH₃ | H | H | H | CH(CH₃)₂ | H | NH-butyl | |
| 2.36 | CH₃ | H | H | H | CH(CH₃)₂ | H | NH-pentyl | |
| 2.37 | CH₃ | H | H | H | CH(CH₃)₂ | H |  (piperidine) | |
| 2.38 | CH₃ | H | H | H | C₃H₇ | H |  (pyrrole) | m.p.: 113° C. |
| 2.39 | CH₃ | H | H | H | C₃H₇ | H | NCH₃CH₂—C₆H₅ | |
| 2.40 | CH₃ | H | H | H | C₃H₇ | H |  (N-methylpiperazine) | ¹H-NMR (CDCl₃): d 8.16 t 7.66 d 7.19 s 6.36 t 3.76 t 2.73 s 2.71 t 2.50 s 2.36 dq 1.76 t 1.00 [ppm] |
| 2.41 | CH₃ | H | H | H | CH(CH₃)₂ | H | 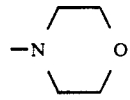 (morpholine) | ¹H-NMR (CDCl₃): d 8.19 t 7.69 d 7.19 s 6.35 m 3.86–3.70 sep 3.05 s 2.69 d 1.31 [ppm] |

-continued

| No. | | | | | | | | |
|---|---|---|---|---|---|---|---|---|
| 2.42 | CH₃ | H | H | H | CH(CH₃)₂ | H | —N(piperazine)N—CH₃ | m.p.: 105° C. |
| 2.43 | CH₃ | H | H | H | CH(CH₃)₂ | H | NH—C₆H₄-4-Cl | m.p.: 128–129° C. |
| 2.44 | CH₃ | H | H | H | C₃H₇ | H | —N(piperazine)NH | m.p.: 180° C. |
| 2.45 | CH₃ | H | H | H | C₅H₉ | H | —N(morpholine)O | m.p.: 143–144° C. |
| 2.46 | CH₃ | H | H | H | C₅H₉ | H | —N(2,6-dimethylmorpholine)O | m.p.: 162° C. |
| 2.47 | CH₃ | H | H | H | C₅H₉ | H | NHCHCH₃C₂H₅ | m.p.: 99–102° C. |
| 2.48 | CH₃ | H | H | H | C₅H₉ | H | NHCH₂C₆H₅ | m.p.: 111° C. |
| 2.49 | CH₃ | H | H | H | C₅H₉ | H | NH—cyclopropyl | m.p.: 124–126° C. |
| 2.50 | CH₃ | H | H | H | C₅H₉ | H | NHCH₂CH=CH₂ | m.p.: 133° C. |
| 2.51 | CH₃ | H | H | H | C₅H₉ | H | —N(piperazine)N—CH₃ | ¹H-NMR (CDCl₃) d 8.15 t 7.66 d 7.21 s 6.36 t 3.77 m 2.90–2.67 s 2.69 t 2.50 s 2.31 m 1.90–1.59 m 1.52–1.20 t 0.85 [ppm] |
| 2.52 | CH₃ | H | H | H | CH₃ | Cl | N(morpholine)O | m.p.: 72–74° C. |
| 2.53 | CH₃ | H | H | H | CH₃ | Cl | N(piperazine)N—CH₃ | m.p.: 80–83° C. |
| 2.54 | CH₃ | H | H | H | CH₃ | Cl | N(2,6-dimethylmorpholine)O | m.p.: 95–97° C. |
| 2.55 | CH₃ | H | H | H | C₃H₇ | H | NHCH₂CH₂N(CH₃)₂ | ¹H-NMR (CDCl₃): d 8.19 t 7.66 d 7.19 s 6.16 s 2.69 m 1.78 t 0.99 |
| 2.56 | CH₃ | H | H | H | CH₃ | H | NHCH₂CH₂OH | |
| 2.57 | CH₃ | H | H | H | CH₃ | Cl | NHCH₂CH₂OCH₃ | |
| 2.58 | CH₃ | H | H | H | (CH₃)₂CH | H | NCH₂CH₂N(piperidine) | |
| 2.59 | CH₃ | H | H | H | C₄H₉ | Br | NHCH₂CH₂SCH₃ | |
| 3.1 | CH₃ | H | H | H | C₆H₅ | H | NHMe | ¹H-NMR (CDCl₃): d 8.41 m 8.14 t 7.71 m 7.47 d 7.21 s 6.70 s 3.04 s 2.72 [ppm] |
| 3.2 | CH₃ | H | H | H | C₆H₅ | H | NEt₂ | ¹H-NMR (CDCl₃): d 8.26 m 8.10 t 7.69 m 7.45 d 7.20 s 6.75 q 3.69 t 2.71 t 1.27 [ppm] |

-continued

| | | | | | | | | |
|---|---|---|---|---|---|---|---|---|
| 3.3 | CH₃ | H | H | H | C₆H₅ | H |  | m.p.: 120–122° C. |
| 3.4 | CH₃ | H | H | H | C₆H₅ | H | NHBu | m.p.: 119–121° C. |
| 3.5 | CH₃ | H | H | H | C₆H₅ | H | NHPr | m.p.: 127–129° C. |
| 3.6 | CH₃ | H | H | H | C₆H₅ | H | NH iso-propyl | m.p.: 105° C. |
| 3.7 | CH₃ | H | H | H | C₆H₅ | H |  | m.p.: 134° C. |
| 3.8 | CH₃ | H | H | H | C₆H₅ | H |  | m.p.: 131° C. |
| 3.9 | CH₃ | H | H | H | 4-CH₃—C₆H₄ | H | NH-propyl | |
| 3.10 | CH₃ | H | H | H | 2,4-(CH₃)₂—C₆H₃ | Br | NH butyl | |
| 3.11 | CH₃ | H | H | H | 2,6-(CH₃)₂—C₆H₃ | Br | NHEt | |
| 3.12 | CH₃ | H | H | H | 3-Et—C₆H₄ | H | 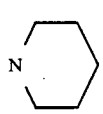 | |
| 3.13 | CH₃ | H | H | H | 3-Cl—C₆H₄ | H | NH propyl | |
| 3.14 | CH₃ | H | H | H | 2,4-Cl₂—C₆H₃— | H | NHMe | |
| 3.15 | CH₃ | H | H | H | 4-OCH₃—C₆H₄— | H | NMe₂ | |
| 4.1 | CH₃ | H | H | H | propyl | Br | NH propyl | |
| 4.2 | CH₃ | H | H | H | propyl | Br | NMe₂ | |
| 4.3 | CH₃ | H | H | H | propyl | Br | NEt₂ | |
| 4.4 | CH₃ | H | H | H | propyl | Br | NHEt | |
| 4.5 | CH₃ | H | H | H | propyl | Br | 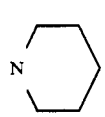 | |
| 4.6 | CH₃ | H | H | H | propyl | Br | NH butyl | |
| 4.7 | CH₃ | H | H | H | propyl | Cl | NH propyl | |
| 4.8 | CH₃ | H | H | H | propyl | Cl | NH iso-propyl | |
| 4.9 | CH₃ | H | H | H | propyl | Cl | 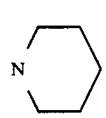 | |
| 4.10 | CH₃ | H | H | H | propyl | Cl | NCH₃CH₂C₆H₅ | |
| 5.1 | CH₃ | H | H | H | CH₂C₆H₅ | H | NEt₂ | ¹H-NMR (CDCl₃): d 8.16 t 7.66 m 7.29 d 7.19 s 5.94 s 4.19 t 3.48 s 2.7 t 1.12 [ppm] |
| 5.2 | CH₃ | H | H | H | CH₂C₆H₅ | H | 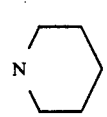 | ¹H-NMR (CDCl₃): d 8.17 t 7.66 m 7.30 d 7.18 s 6.10 s 4.12 m 3.57 s 2.70 m 1.60 [ppm] |
| 5.3 | CH₃ | H | H | H | CH₂C₆H₅ | H | NH propyl | ¹H-NMR (CDCl₃): d 8.19 t 7.68 m 7.30 d 7.19 s 5.94 s 4.09 t 3.16 s 2.69 m 1.61 t 0.92 [ppm] |
| 5.4 | CH₃ | H | H | H | CH₂C₆H₅ | H | NHEt | |
| 5.5 | CH₃ | H | H | H | CH₂C₆H₅ | H | NH butyl | |
| 5.6 | CH₃ | H | H | H | CH₂C₆H₅ | H | 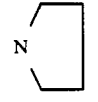 | |
| 5.7 | CH₃ | H | H | H | CH₂C₆H₅ | H | NMe₂ | |

-continued

| | | | | | | | | |
|---|---|---|---|---|---|---|---|---|
| 5.8 | CH₃ | H | H | H | CH₂C₆H₅ | H | 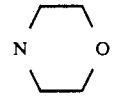 N__O | m.p.: 161-163° C. |
| 5.9 | CH₃ | H | H | H | CH₂C₆H₅ | H | NH pentyl | |
| 5.10 | CH₃ | H | H | H | CH₂C₆H₅ | H | 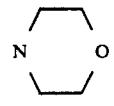 N__O | ¹-HNMR (CDCl₃): d 8.17 t 7.68 s 7.23 d 7.19 s 6.09 s 4.16 m 3.84-3.52 s 2.70 [ppm] |
| 5.11 | CH₃ | H | H | H | CH₂C₆H₅ | H | 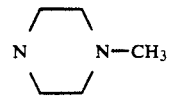 N__N—CH₃ | ¹H-NMR (CDCl₃): d 8.18 t 7.68 s 7.29 d 7.19 s 6.12 t 4.18 t 3.64 s 2.70 t 2.43 s 2.30 [ppm] |
| 5.12 | CH₃ | H | H | H | CH₂C₆H₅ | H | NHC₆H₄-4-Cl | m.p.: 172-174° C. |
| 6.1 | CH₃ | H | H | H | CH₂OC₆H₅ | H | NHEt₂ | ¹H-NMR (CDCl₃): d 8.21 t 7.71 m 7.24 m 6.98 s 6.60 s 5.23 q 3.59 s 2.72 t 1.19 [ppm] |
| 6.2 | CH₃ | H | H | H | CH₂OC₆H₅ | H | 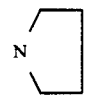 N_ | m.p.: 122° C. |
| 6.3 | CH₃ | H | H | H | CH₂OC₆H₅ | H | NMe₂ | m.p.: 134° C. |
| 6.4 | CH₃ | H | H | H | CH₂CH₂-cyclopentyl | H | 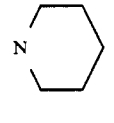 N_ | ¹H-NMR (CDCl₃): d 8.16 t 7.64 d 7.17 s 6.35 s 2.6 m 1.65 m 1.20 [ppm] |
| 6.5 | CH₃ | H | H | H | CH₂CH₂-cyclopentyl | H | NH propyl | ¹H-NMR (CDCl₃): d 8.15 t 7.62 d 7.16 s 6.16 t 3.26 s 2.63 m 1.71 t 0.97 [ppm] |
| 6.6 | CH₃ | H | H | H | CH₂CH₂-cyclopentyl | H | NHMe | ¹H-NMR (CDCl₃): d 8.19 t 7.69 d 1.9 s 6.19 q 5.60 d 2.94 s 2.66 m 1.69 [ppm] |
| 6.7 | CH₃ | H | H | H | CH₂CH₂-cyclopentyl | H | NCH₃CH₂C₆H₅ | ¹H-NMR (CDCl₃): d 8.14 t 7.64 m 7.26 d 7.16 s 6.31 s 4.89 s 3.13 s 2.70 m 1.62 [ppm] |
| 6.8 | CH₃ | H | H | H | CH₂OC₆H₅ | H | NH propyl | m.p.: 152-153° C. |
| 6.9 | CH₃ | H | H | H | CH₂CH₂ cyclopentyl | H | 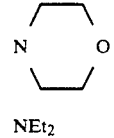 N__O | m.p.: 98-100° C. |
| 6.10 | CH₃ | H | H | H | CH₂OC₆H₅ | H | NEt₂ | m.p.: 142° C. |
| 6.11 | CH₃ | H | H | H | CH₂OC₆H₅ | H | 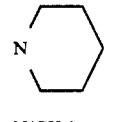 N_ | m.p.: 122-123° C. |
| 6.12 | CH₃ | H | H | H | CH₂OC₆H₅ | H | N(CH₃)₂ | m.p.: 134-136° C. |
| 6.13 | CH₃ | H | H | H | CH₂OC₆H₅ | H | 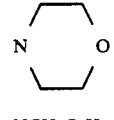 N__O | m.p.: 125° C. |
| 6.14 | CH₃ | H | H | H | CH₂OC₆H₅ | H | NCH₃C₆H₅ | m.p.: 109° C. |
| 7.1 | CH₃ | H | H | H | CH₃ | Cl | NEt₂ | ¹H-NMR (CDCl₃): d 8.11 t 7.66 d 7.18 q 3.69 s 2.70 s 2.66 t 1.33 [ppm] |
| 7.2 | CH₃ | H | H | H | CH₃ | Cl | NMe₂ | ¹H-NMR (CDCl₃): d 8.16 t 7.68 d 7.19 q 3.26 s 2.70 s 2.64 [ppm] |
| 7.3 | CH₃ | H | H | H | CH₃ | Cl | NH propyl | m.p.: 106-107 |

-continued

| | | | | | | | | |
|---|---|---|---|---|---|---|---|---|
| 7.4 | CH₃ | H | H | H | CF₃ | H | NH propyl | |
| 7.5 | CH₃ | H | H | H | CF₃ | H | NH butyl | |
| 7.6 | CH₃ | H | H | H | MeOCH₂ | OCH₃ |  (pyrrolidine) | |
| 7.7 | CH₃ | H | H | H | MeOCH₂ | OCH₃ | NHC₃H₇ | ¹H-NMR (CDCl₃): d 8.14 t 7.64 d 7.16 s 4.56 s 3.81 s 3.46 s 2.64 [ppm] |
| 7.8 | CH₃ | H | H | H | MeOCH₂ | OCH₃ | NEt₂ | ¹H-NMR (CDCl₃): d 8.08 t 7.64 d 7.16 s 4.59 q 3.67 s 3.49 s 2.66 t 1.24 [ppm] |
| 7.9 | CH₃ | H | H | H | MeOCH₂ | OCH₃ | NHC₆H₅ | |
| 7.10 | CH₃ | H | H | H | H₃COCH₂ | OCH₃ | NHC₂H₅ | m.p.: 102° C. |
| 7.11 | CH₃ | H | H | H | H₃COCH₂ | OCH₃ | NHCH₂C₆H₅ | m.p.: 120–121° C. |
| 7.12 | CH₃ | H | H | H | H₃COCH₂ | OCH₃ |  (piperidine) | m.p.: 129° C. |
| 7.13 | CH₃ | H | H | H | C₃H₇ | Br | NHC₃H₇ | m.p.: 77° C. |
| 7.14 | CH₃ | H | H | H | C₃H₇ | Br | N(C₂H₅)₂ | m.p.: 95° C. |
| 7.15 | CH₃ | H | H | H | C₃H₇ | Br |  (morpholine) | m.p.: 89° C. |
| 7.16 | CH₃ | H | H | H | C₃H₇ | Br | N(CH₃)₂ | m.p.: 103° C. |
| 7.17 | CH₃ | H | H | H | C₃H₇ | Br |  (N-methylpiperazine) | |
| 7.18 | CH₃ | H | H | H | CH₃ | Cl |  (morpholine) | m.p.: 72–74° C. |
| 7.19 | CH₃ | H | H | H | CH₃ | Cl |  (N-methylpiperazine) | m.p.: 80–83° C. |
| 7.20 | CH₃ | H | H | H | CH₃ | Cl |  (2,6-dimethylmorpholine) | m.p.: 95–97° C. |
| 8.1 | CH₃ | H | H | H | —(CH₂)₄— | | NHCH₃ | ¹H-NMR (CDCl₃): d 8.21 t 7.66 d 7.17 s 3.14 m 2.91 s 2.66 m 2.35 m 1.84 [ppm] |
| 8.2 | CH₃ | H | H | H | —(CH₂)₄— | |  (morpholine) | ¹H-NMR (CDCl₃): d 8.14 t 7.68 d 7.17 m 3.85 m 3.47 m 3.05 s 2.68 m 2.59 m 1.86 [ppm] |
| 8.3 | CH₃ | H | H | H | —(CH₂)₄— | |  (pyrrolidine) | ¹H-NMR (CDCl₃): d 8.16 t 7.64 d 7.15 m 3.71 t 2.97 t 2.78 s 2.66 m 1.86 [ppm] |
| 8.4 | CH₃ | H | H | H | —(CH₂)₄— | | NH propyl | m.p.: 170–172° C. |
| 8.5 | CH₃ | H | H | H | —(CH₂)₄— | | NEt₂ | m.p.: 153–154° C. |

-continued

| No. | | | | | | | | Physical data |
|---|---|---|---|---|---|---|---|---|
| 8.6 | CH$_3$ | H | H | H | —(CH$_2$)$_4$— | | 2,6-dimethylmorpholin-N-yl | m.p.: 141–144° C. |
| 8.7 | CH$_3$ | H | H | H | —(CH$_2$)$_4$— | | NHCH$_2$C≡C—H | |
| 8.8 | CH$_3$ | H | H | H | —(CH$_2$)$_4$— | | NCH$_3$CH$_2$C$_6$H$_5$ | |
| 9.1 | CH$_3$ | H | H | H | H | OCH$_3$ | NH propyl | |
| 9.2 | CH$_3$ | H | H | H | H | OCH$_3$ | pyrrolidin-N-yl | |
| 9.3 | CH$_3$ | H | H | H | H | H | NH butyl | |
| 9.4 | CH$_3$ | H | H | H | H | H | NH propyl | |
| 9.5 | CH$_3$ | H | H | H | Cl | H | NEt$_2$ | $^1$H-NMR (CDCl$_3$): d 8.14 t 7.54 d 7.20 s 6.38 q 3.58 s 2.68 t 1.23 [ppm] |
| 9.6 | CH$_3$ | H | H | H | Cl | H | piperidin-N-yl | |
| 9.7 | CH$_3$ | H | H | H | Cl | OCH$_3$ | NH pentyl | |
| 9.8 | CH$_3$ | H | H | H | NH propyl | H | NH propyl | |
| 9.9 | CH$_3$ | H | H | H | NHEt | H | NH propyl | |
| 9.10 | CH$_3$ | H | H | H | OC$_4$H$_9$ | H | NHEt | |
| 9.11 | CH$_3$ | H | H | H | OCH$_3$ | H | NEt$_2$ | |
| 9.12 | CH$_3$ | H | H | H | SMe | H | NHMe | |
| 9.13 | CH$_3$ | H | H | H | S—C$_6$H$_4$-4-Cl | CH$_3$ | NH butyl | |
| 9.14 | CH$_3$ | H | H | H | H | Et | NH propyl | |
| 9.15 | CH$_3$ | H | H | H | H | CH$_3$ | NH propyl | |
| 9.16 | CH$_3$ | H | H | H | NHC$_3$H$_7$ | H | NEt$_2$ | m.p.: 79–81° C. |
| 9.17 | CH$_3$ | H | H | H | Cl | H | NEt$_2$ | $^1$H-NMR (CDCl$_3$): d 8.14 t 7.68 d 7.21 s 6.37 q 3.56 s 2.67 t 1.20 [ppm] |
| 9.18 | CH$_3$ | H | H | H | Cl | H | morpholin-N-yl | m.p.: 159° C. |
| 9.19 | CH$_3$ | H | H | H | OC$_2$H$_5$ | H | NHC$_3$H$_7$ | m.p.: 135° C. |
| 10.1 | C$_6$H$_5$ | H | H | H | CH$_3$ | H | NMe$_2$ | $^1$H-NMR (CDCl$_3$): dd 8.36 s 6.30 s 3.22 s 2.51 [ppm] |
| 10.2 | C$_6$H$_5$ | H | H | H | CH$_3$ | H | NEt$_2$ | $^1$H-NMR (CDCl$_3$): dd 8.32 s 6.26 q 3.62 s 2.51 t 1.23 [ppm] |
| 10.3 | C$_6$H$_5$ | H | H | H | CH$_3$ | H | NH propyl | $^1$H-NMR (CDCl$_3$): dd 8.33 s 6.19 t 3.24 s 2.47 m 1.65 t 0.98 [ppm] |
| 10.4 | C$_6$H$_5$ | H | H | H | CH$_3$ | H | NH iso-propyl | $^1$H-NMR (CDCl$_3$): dd 8.39 s 6.17 sept 3.92 s 2.50 d 1.28 [ppm] |
| 10.5 | C$_6$H$_5$ | H | H | H | CH$_3$ | CH$_3$ | NH-(3,5-Cl$_2$—C$_6$H$_3$) | |
| 11.1 | C$_6$H$_5$ | H | H | H | C$_3$H$_7$ | H | NEt$_2$ | $^1$H-NMR (CDCl$_3$): dd 8.28 s 6.21 q 3.61 t 2.73 m 1.80 t 1.24 t 1.02 [ppm] |
| 11.2 | C$_6$H$_5$ | H | H | H | C$_3$H$_7$ | H | NH propyl | $^1$H-NMR (CDCl$_3$): dd 8.31 s 6.15 t 5.28 m 3.27 t 2.70 m 1.72 t 1.01 t 1.03 [ppm] |
| 11.3 | C$_6$H$_5$ | H | H | H | C$_3$H$_7$ | H | NMe$_2$ | $^1$H-NMR (CDCl$_3$): dd 8.33 s 6.26 s 3.20 t 2.76 m 1.82 t 1.00 [ppm] |
| 11.4 | C$_6$H$_5$ | H | H | H | C$_3$H$_7$ | H | NH—CH$_2$—CH=CH$_2$ | |
| 11.5 | C$_6$H$_5$ | H | H | H | C$_3$H$_7$ | H | NHCH$_2$—CH=CH—CH$_3$ E isomer | |
| 11.6 | C$_6$H$_5$ | H | H | H | C$_3$H$_7$ | CH$_3$ | NHCH$_2$—CH=CH—CH$_3$ Z isomer | |
| 20.1 | H | H | H | H | C$_6$H$_5$ | H | NEt$_2$ | m.p.: 155–156° C. |
| 20.2 | H | H | H | H | C$_6$H$_5$ | H | piperidin-N-yl | $^1$H-NMR (CDCl$_3$): d 8.81 d 8.49 m 8.10 t 7.81 m 7.41 s 6.73 q 3.69 t 1.26 [ppm] |

-continued

| | | | | | | | | |
|---|---|---|---|---|---|---|---|---|
| 20.3 | H | H | H | H | C6H5 | H | NH propyl | m.p.: 118–120° C. |
| 20.4 | H | H | H | H | C6H5 | H | NH iso-propyl | |
| 20.5 | H | H | H | H | C6H5 | H | NHMe | |
| 20.6 | H | H | H | H | C6H5 | H | 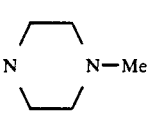 | |
| 20.7 | H | H | H | H | C6H5 | H | NMe2 | |
| 20.8 | H | H | H | H | C6H5 | H | 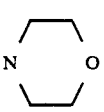 | m.p.: 189–190° C. |
| 20.9 | H | H | H | H | CH3 | H | NHC3H7 | m.p.: 146° C. |
| 20.10 | H | H | H | H | CH3 | H | NHCH2CH(CH3)2 | m.p.: 123° C. |
| 20.11 | H | H | H | H | CH3 | H |  | m.p.: 82° C. |
| 20.12 | H | H | H | H | CH3 | H | NHCH(CH3)2 | m.p.: 115–117° C. |
| 30.1 | 4-Cl—C6H4—OCH2 | H | H | H | CH3 | H | NMe2 | $^1$H-NMR (CDCl3): d 8.34 t 7.85 d 7.56 d 7.23 d 6.92 s 6.32 |
| 30.2 | 4-Cl—C6H4—OCH2 | H | H | H | CH3 | H | NEt2 | $^1$H-NMR (CDCl3): d 8.30 t 7.81 d 7.53 d 7.22 d 6.92 s 6.25 s 5.39 q 3.62 t 2.52 t 1.23 [ppm] |
| 30.3 | 4-Cl—C6H4—OCH2 | H | H | H | CH3 | H | NH propyl | |
| 30.4 | C6H5—OCH2 | H | H | H | CH3 | H | NHEt | |
| 30.5 | 2,6-(Me)2—C6H3 | H | H | H | CH3 | H |  | |
| 31.1 | 4-Cl—C6H4—OCH2 | H | H | H | propyl | H | NEt2 | $^1$H-NMR (CDCl3): d 8.29 t 7.81 d 7.54 d 7.24 d 6.93 s 6.24 s 5.36 q 3.6 t 2.74 m 1.81 t 1.25 t 1.02 [ppm] |
| 31.2 | 4-Cl—C6H4—OCH2 | H | H | H | propyl | H | NMe2 | $^1$H-NMR (CDCl3): d 8.31 t 7.81 d 7.54 d 7.23 d 6.93 s 6.30 s 5.34 s 3.19 t 2.74 m 1.83 t 1.01 [ppm] |
| 31.3 | 4-Cl—C6H4—OCH2 | H | H | H | propyl | H | NH propyl | $^1$H-NMR (CDCl3): d 8.31 t 7.82 d 7.55 d 7.24 d 6.91 d 6.18 s 5.34 m 3.26 t 2.71 m 1.70 t 1.01 [ppm] |
| 31.4 | 4-Cl—C6H4—OCH2 | H | H | H | propyl | H | NCH3C6H5 | m.p.: 139–140° C. |
| 40.1 | 4-Cl—C6H4—O—C6H4—OCH2 | H | H | H | CH3 | H | NEt2 | $^1$H-NMR (DMSO-d6): d 8.21 t 7.92 d 7.58 d 7.37 dd 7.09 d 6.94 s 6.51 s 5.28 q 3.58 s 2.35 t 1.14 [ppm] |
| 41.1 | 4-Cl—C6H4—O—C6H4—OCH2 | H | H | H | propyl | H | NEt2 | $^1$H-NMR (DMSO-d6): d 8.21 t 7.94 d 7.60 d 7.39 dd 7.09 d 6.94 s 6.50 s 5.23 q 3.59 t 2.63 m 1.71 t 1.15 t 0.96 [ppm] |
| 50.1 | C6H5CH2 | H | H | H | propyl | H | NHC6H5 | m.p.: 116° C. |
| 50.2 | C6H5CH2 | H | H | H | propyl | H | NCH3C6H5 | |
| 50.3 | C6H5CH2 | H | H | H | propyl | H | NH propyl | |
| 50.4 | C6H5CH2 | H | H | H | propyl | H | NH pentyl | |
| 50.5 | C6H5CH2 | H | H | H | propyl | H | 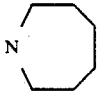 | |
| 50.6 | C6H5CH2 | H | H | H | iso-propyl | H | NH propyl | |
| 50.7 | C6H5CH2 | H | H | H | iso-propyl | H | NEt2 | |

| | | | | | | | | |
|---|---|---|---|---|---|---|---|---|
| 50.8 | C₆H₅CH₂ | H | H | H | iso-propyl | H |  | |
| 50.9 | C₆H₅CH₂ | H | H | H | iso-propyl | H | 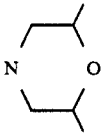 | |
| 50.10 | C₆H₅CH₂ | H | H | H | C₃H₇ | H | N(C₂H₅)₂ | m.p.: 98° C. |
| 50.11 | C₆H₅CH₂ | H | H | H | C₃H₇ | H | NHC₃H₇ | m.p.: 127° C. |
| 50.12 | C₆H₅CH₂ | H | H | H | C₃H₇ | H | N(CH₃)₂ | m.p.: 154° C. |
| 50.13 | C₆H₅CH₂ | H | H | H | C₃H₇ | H |  | m.p.: 115–117° C. |
| 50.14 | C₆H₅CH₂ | H | H | H | C₃H₇ | H |  | m.p.: 162–163° C. |
| 50.15 | C₆H₅CH₂ | H | H | H | C₃H₇ | H | 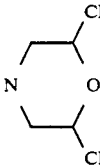 | m.p.: 164° C. |
| 50.16 | C₆H₅CH₂ | H | H | H | C₃H₇ | H | 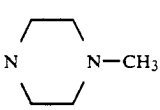 | m.p.: 134° C. |
| 50.17 | C₆H₅CH₂ | H | H | H | C₃H₇ | H |  | m.p.: 170° C. |
| 51.1 | C₆H₅CH₂ | H | H | H | C₆H₅ | H | NHC₃H₇ | m.p.: 147–148° C. |
| 51.2 | C₆H₅CH₂ | H | H | H | C₆H₅ | H | N(C₂H₅)₂ | m.p.: 119° C. |
| 51.3 | C₆H₅CH₂ | H | H | H | C₆H₅ | H |  | m.p.: 99–101° C. |
| 52.1 | C₆H₅CH₂ | H | H | H | C₅H₉ | H |  | m.p.: 139° C. |
| 52.2 | C₆H₅CH₂ | H | H | H | C₅H₉ | H | NHC₃H₇ | m.p.: 147° C. |
| 52.3 | C₆H₅CH₂ | H | H | H | C₅H₉ | H | NHCH₂CH=CH₂ | m.p.: 121–123° C. |
| 52.4 | C₆H₅CH₂ | H | H | H | C₅H₉ | H | NHC₅H₉ | m.p.: 133° C. |
| 52.5 | C₆H₅CH₂ | H | H | H | C₅H₉ | H | 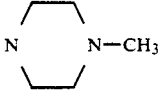 | ¹H-NMR (CDCl₃): d 8.16 t 7.64 m 7.37–7.18 d 8.01 s 6.38 s 4.35 t 3.78 m 2.90–2.74 t 2.52 m 1.91–1.60 m 1.50–1.19 m 1.02–0.76 [ppm] |
| 53.1 | C₆H₅CH₂ | H | H | H | C₆H₅CH₂ | H | NHC₃H₇ | m.p.: 149° C. |
| 53.2 | C₆H₅CH₂ | H | H | H | C₆H₅CH₂ | H | NHCHCH₃C₂H₅ | m.p.: 162° C. |

-continued

| | | | | | | | | |
|---|---|---|---|---|---|---|---|---|
| 53.3 | C6H5CH2 | H | H | H | C6H5CH2 | H | 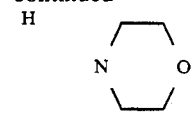 | m.p.: 114–116° C. |
| 53.4 | C6H5CH2 | H | H | H | C6H5CH2 | H | NHCH2CH=CH2 | m.p.: 130–133° C. |
| 53.5 | C6H5CH2 | H | H | H | C6H5CH2 | H | NHCH2C6H5 | m.p.: 145° C. |
| 71.1 | H3COCH2 | H | H | H | propyl | H | 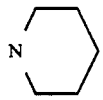 | $^1$H-NMR (CDCl3): d 8.24 t 7.80 d 7.49 s 6.35 s 4.76 m 3.69 t 2.71 m 1.65 t 0.97 [ppm] |
| 71.2 | H3COCH2 | H | H | H | propyl | H | NH propyl | |
| 71.3 | H3COCH2 | H | H | H | iso-propyl | H | NH propyl | |
| 71.4 | CH3OCH2 | H | H | H | propyl | H | NCH2C6H5 | |
| 71.5 | CH3OCH2 | H | H | H | propyl | H | 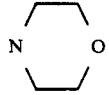 | m.p.: 116–117° C. |
| 72.1 | H3COCH2 | H | H | H | C6H5 | H | NH propyl | $^1$H-NMR (CDCl3): d 8.50 m 8.13 t 7.85 m 7.49 s 6.71 s 4.79 s 3.49 m 3.36 m 1.72 t 1.04 [ppm] |
| 72.2 | H3COCH2 | H | H | H | C6H5 | H | NEt2 | $^1$H-NMR (CDCl3): d 8.35 m 8.11 t 7.82 m 7.46 s 6.74 s 4.78 q 3.68 s 3.49 t 1.24 [ppm] |
| 72.3 | H3COCH2 | H | H | H | C6H5 | H |  | m.p.: 147–148° C. |
| 80.1 | C3H7 | H | H | H | C3H7 | H | NH propyl | |
| 80.2 | C3H7 | H | H | H | C3H7 | H | 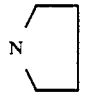 | |
| 80.3 | C3H7 | H | H | H | C3H7 | H | NMe2 | |
| 80.4 | C3H7 | H | H | H | CH(CH3)2 | H | NH butyl | |
| 80.5 | C3H7 | H | H | H | CH(CH3)2 | H | NH propyl | |
| 80.6 | C3H7 | H | H | H | CH(CH3)2 | H | NHEt | |
| 80.7 | C3H7 | H | H | H | C6H5 | H | NH butyl | |
| 90.1 | CH3 | H | CH3 | H | propyl | H | NH propyl | |
| 90.2 | CH3 | H | CH3 | H | propyl | H | NHEt | |
| 90.3 | CH3 | H | CH3 | H | propyl | H | NMe2 | |
| 90.4 | CH3 | H | CH3 | H | iso-propyl | H | 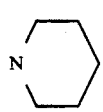 | |
| 100.1 | H | H | Et | H | propyl | H | NH propyl | |
| 100.2 | H | H | Et | H | propyl | H | 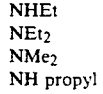 | |
| 100.3 | H | H | Et | H | propyl | H | NH-iso-propyl | |
| 100.4 | H | H | Et | H | C6H5 | H | NHEt | |
| 100.5 | H | H | Et | H | C6H5 | H | NEt2 | |
| 100.6 | H | H | Et | H | C6H5 | H | NMe2 | |
| 100.7 | H | H | Et | H | iso-propyl | H | NH propyl | |
| 100.8 | H | H | Et | H | iso-propyl | H | NMe2 | |
| 101.1 | CH3 | CH3 | H | H | propyl | H | NH propyl | m.p.: 108° C. |
| 101.2 | CH3 | CH3 | H | H | propyl | H | NHMe | m.p.: 127–128° C. |

-continued

| | | | | | | | | |
|---|---|---|---|---|---|---|---|---|
| 101.3 | CH₃ | CH₃ | H | H | C₃H₇ | H | 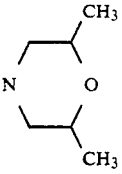 2,6-dimethylmorpholino | m.p.: 133° C. |
| 101.4 | CH₃ | CH₃ | H | H | C₃H₇ | H | 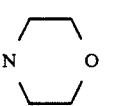 morpholino | m.p.: 125° C. |
| 101.5 | CH₃ | CH₃ | H | H | C₃H₇ | H | 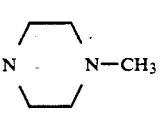 4-methylpiperazino | m.p.: 87° C. |
| 101.6 | CH₃ | CH₃ | H | H | C₆H₅CH₂ | | 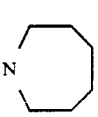 heptamethyleneimino | m.p.: 56° C. |
| 101.7 | CH₃ | CH₃ | H | H | C₆H₅CH₂ | | NHC₅H₁₁ | m.p.: 111° C. |
| 101.8 | CH₃ | CH₃ | H | H | C₆H₅CH₂ | | 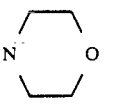 morpholino | m.p.: 127° C. |
| 101.9 | CH₃ | CH₃ | H | H | —(CH₂)₄— | | NHC₃H₇ | m.p.: 80° C. |
| 101.10 | CH₃ | CH₃ | H | H | —(CH₂)₄— | | 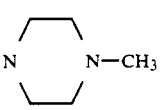 4-methylpiperazino | m.p.: 155° C. |
| 101.11 | CH₃ | CH₃ | H | H | —(CH₂)₄— | | NHC₅H₁₁ | m.p.: 86-88° C. |
| 102.1 | propyl | H | H | H | H | C₆H₅ | NEt₂ | m.p.: 96° C. |
| 102.2 | propyl | H | H | H | H | C₆H₅ | NHEt | m.p.: 112-113° C. |
| 102.3 | C₃H₇ | H | H | H | C₆H₅CH₂ | H | NHC₃H₇ | m.p.: 139° C. |
| 102.4 | C₃H₇ | H | H | H | C₆H₅CH₂ | H | 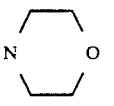 morpholino | m.p.: 185° C. |
| 102.5 | C₃H₇ | H | H | H | C₆H₅CH₂ | H | 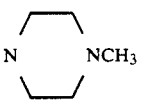 4-methylpiperazino | m.p.: 135-136° C. |
| 102.6 | C₃H₇ | H | H | H | C₆H₅CH₂ | H | NHC₅H₁₁ | m.p.: 112° C. |
| 102.7 | C₃H₇ | H | H | H | C₆H₅CH₂ | H | NHCH₂C₆H₅ | m.p.: 156-159° C. |
| 102.8 | C₃H₇ | H | H | H | (CH₂)₂-cyclopentyl | H | NHC₃H₇ | m.p.: 112-114° C. |
| 102.9 | C₃H₇ | H | H | H | (CH₂)₂-cyclopentyl | H | 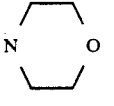 morpholino | m.p.: 174° C. |
| 102.10 | C₃H₇ | H | H | H | (CH₂)₂-cyclopentyl | H | 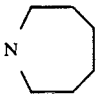 heptamethyleneimino | m.p.: 170° C. |
| 102.11 | C₃H₇ | H | H | H | (CH₂)₂-cyclopentyl | H | NHCH₂CH=CH₂ | m.p.: 141-143° C. |

-continued

| | | | | | | | | |
|---|---|---|---|---|---|---|---|---|
| 102.12 | C₃H₇ | H | H | H | (CH₂)₂-cyclopentyl | H | 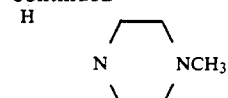 N-piperazine-NCH₃ | m.p.: 158–160° C. |
| 102.13 | C₃H₇ | H | H | H | CH₃OCH₂ | OCH₃ | NHC₃H₇ | m.p.: 87–89° C. |
| 102.14 | C₃H₇ | H | H | H | CH₃OCH₂ | OCH₃ | morpholino | m.p.: 135° C. |
| 102.15 | C₃H₇ | H | H | H | CH₃OCH₂ | OCH₃ | N-methylpiperazine | m.p.: 121–122° C. |
| 102.16 | C₃H₇ | H | H | H | CH₃ | Cl | NHC₃H₇ | m.p.: 99° C. |
| 102.17 | C₃H₇ | H | H | H | CH₃ | Cl | morpholino | m.p.: 161° C. |
| 102.18 | C₃H₇ | H | H | H | CH₃ | Cl | NHCH₂CH=CH₂ | m.p.: 128° C. |
| 102.19 | C₃H₇ | H | H | H | CH₃ | Cl | NHC₅H₁₁ | m.p.: 112° C. |
| 102.20 | C₃H₇ | H | H | H | C₃H₇ | N | 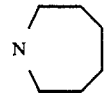 hexamethyleneimino | m.p.: 61–63° C. |
| 102.21 | C₃H₇ | H | H | H | C₃H₇ | H | NHC₅H₁₁ | m.p.: 75° C. |
| 102.22 | C₃H₇ | H | H | H | C₃H₇ | H | NHC₃H₇ | m.p.: 86–89° C. |
| 102.23 | C₃H₇ | H | H | H | C₃H₇ | H | 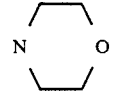 morpholino | m.p.: 75° C. |
| 102.24 | C₃H₇ | H | H | H | C₃H₇ | H | 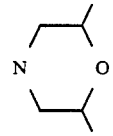 dimethylmorpholino | m.p.: 66–68° C. |
| 102.25 | C₃H₇ | H | H | H | C₃H₇ | N | NHCH(CH₃)₂ | m.p.: 98–100° C. |
| 102.26 | C₃H₇ | H | H | H | C₃H₇ | N | 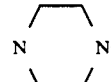 N-methylpiperazine | m.p.: 85° C. |
| 102.27 | C₃H₇ | H | H | H | C₃H₇ | H | 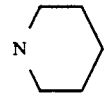 piperidino | m.p.: 109–110° C. |
| 102.28 | C₃H₇ | H | H | H | C₃H₇ | H | NHCH₂C₆H₅ | m.p.: 94° C. |
| 102.29 | C₃H₇ | H | H | H | —(CH₂)₄— | | NHC₃H₇ | m.p.: 135–137° C. |
| 102.30 | C₃H₇ | H | H | H | —(CH₂)₄— | | NHC₅H₁₁ | m.p.: 128–130° C. |
| 102.31 | C₃H₇ | H | H | H | —(CH₂)₄— | | 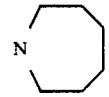 hexamethyleneimino | m.p.: 125–126° C. |
| 102.32 | C₃H₇ | H | H | H | —(CH₂)₄— | | 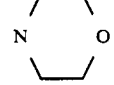 morpholino | m.p.: 111–113° C. |

-continued

| | | | | | | | | |
|---|---|---|---|---|---|---|---|---|
| 102.33 | C₃H₇ | H | H | H | OC₂H₅ | H | NHC₅H₁₁ | |
| 110.1 | H | H | C₆H₅ | H | propyl | H | NHMe | |
| 110.2 | H | H | C₆H₅ | H | propyl | H | NMe₂ | |
| 110.3 | H | H | C₆H₅ | H | propyl | H | NH propyl | |
| 110.4 | H | H | C₆H₅ | H | propyl | H | NH-cyclohexyl | |
| 110.5 | H | H | C₆H₅ | H | propyl | H | piperidinyl | |
| 110.6 | H | H | C₆H₅ | H | iso-propyl | H | NH propyl | |
| 110.7 | H | H | C₆H₅ | H | iso-propyl | H | NHEt | |
| 110.8 | H | H | C₆H₅ | H | iso-propyl | H | NH-cyclopropyl | |
| 110.9 | H | H | C₆H₅ | H | iso-propyl | H | N-methylpiperazinyl | |
| 110.10 | H | H | C₆H₅ | H | phenyl | H | NH propyl | |
| 110.11 | H | H | C₆H₅ | H | phenyl | H | NHEt | |
| 110.12 | H | H | C₆H₅ | H | phenyl | H | NH iso-propyl | |
| 110.13 | H | H | C₆H₅ | H | C₃H₇ | H | NHC₅H₁₁ | m.p.: 107° C. |
| 110.14 | H | H | C₆H₅ | H | C₃H₇ | H | morpholinyl | m.p.: 117–119° C. |
| 110.15 | H | H | C₆H₅ | H | C₃H₇ | H | hexamethyleneiminyl | m.p.: 125–126° C. |
| 110.16 | H | H | C₆H₅ | H | C₃H₇ | H | NHCH₂C₆H₅ | m.p.: 132° C. |
| 110.17 | H | H | C₆H₅ | H | C₆H₅CH₂ | H | NHC₃H₇ | m.p.: 139° C. |
| 110.18 | H | H | C₆H₅ | H | C₆H₅CH₂ | H | morpholinyl | m.p.: 140° C. |
| 110.19 | H | H | C₆H₅ | H | C₆H₅CH₂ | H | 2,6-dimethylmorpholinyl | m.p.: 148–150° C. |
| 110.20 | H | H | C₆H₅ | H | C₆H₅CH₂ | H | N-methylpiperazinyl | ¹H-NMR (CDCl₃): d 8.86 s(br) 8.64 m 7.78–7.26 s 6.18 s 4.19 t 3.71 t 2.43 s 2.29 [ppm] |
| 120.1 | CH₃ | H | CH₃ | H | C₃H₇ | H | morpholinyl | m.p.: 155° C. |
| 120.2 | CH₃ | H | CH₃ | H | C₃H₇ | H | 2,6-dimethylmorpholinyl | m.p.: 169–170° C. |

-continued

| Nr. | R¹ | R² | R³ | R⁴ | R⁵ | R⁶ | NR⁷R⁸ | Physical properties |
|---|---|---|---|---|---|---|---|---|
| 120.3 | CH₃ | H | CH₃ | H | C₃H₇ | H | 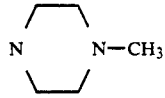 | ¹H-NMR (CDCl₃): s(br) 7.96 s(br) 7.03 s 6.38 t 3.71 t 2.74 s 2.64 t 2.53 s 2.36 dq 1.79 t 0.99 [ppm] |
| 120.4 | CH₃ | H | CH₃ | H | C₃H₇ | H | NHC₃H₇ | m.p.: 86–88° C. |
| 120.5 | CH₃ | H | CH₃ | H | C₃H₇ | H |  | m.p.: 112° C. |
| 120.6 | CH₃ | H | CH₃ | H | C₃H₇ | H | 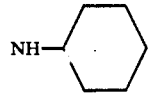 | m.p.: 131° C. |
| 120.7 | CH₃ | H | CH₃ | H | C₆H₅CH₂ | H |  | m.p.: 148° C. |
| 120.8 | CH₃ | H | CH₃ | H | C₆H₅CH₂ | H | 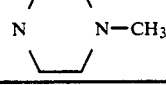 | ¹H-NMR (CDCl₃): s(br) 7.99 s(br) 7.05 s 6.11 s 4.18 t 3.65 s 2.63 t 2.45 s 2.38 s 2.31 [ppm] |

TABLE B
(acid addition salts)

| Nr. | R¹ | R² | R³ | R⁴ | R⁵ | R⁶ | NR⁷R⁸ | Physical properties |
|---|---|---|---|---|---|---|---|---|
| 200.1 | CH₃ | H | H | H | C₆H₅ | H | NH propyl | semi-crystalline, colourless |
| 200.2 | CH₃ | H | H | H | C₃H₇ | H | NH Et | |
| 200.3 | CH₃ | H | H | H | C₃H₇ | Br | NH propyl | |
| 200.4 | C₆H₅ | H | H | H | CH₃ | H | NH butyl | |
| 200.5 | C₃H₇ | H | H | H | CH₂CH₂-cyclopentyl | H | NHEt | |

C. BIOLOGICAL EXAMPLES

Filter paper disks of diameter 6 mm are uniformly wetted with 20 μl portions of the active substances indicated in Table 1 and place on an agar medium whose composition depends on the fungus species. Before this, 0.5 ml of a suspension culture of the test organism (in the present case Botrytis cinerea, BCM- and iprodion-resistant strain, about 10⁵–10⁶ conidia) is added per Petri dish while the agar is still liquid, and the agar plates treated in this manner are subsequently incubated at about 22° C. To measure the inhibition of the fungus, the inhibition zone is measured after an incubation period of 3–4 days and recorded in mm.

TABLE 1
Fungicidal action against *Botrytis cinerea*-BCM-and iprodion-resistant strain.

| Compound according to Example | Inhibition zones in mm diameter at 1000 ppm of active substance and 20 μl per filter disk |
|---|---|
| 1.1 | 28 |
| 1.2 | 26 |
| 1.3 | 30 |
| 1.4 | 24 |
| 2.7 | 32 |
| 2.1 | 12 |
| 2.38 | 12 |
| 2.2 | 44 |
| 7.1 | 14 |
| 7.3 | 40 |
| 10.2 | 14 |
| 11.1 | 22 |
| 11.2 | 20 |
| 11.3 | 22 |
| 31.4 | 16 |
| untreated control | 0 |

EXAMPLE 2

Filter paper disks of diameter 6 nm are uniformly wetted with 20 μl portions of the active substances indicated in Table 2 and placed on an agar medium whose composition depends on the fungus species. Before this, 0.5 ml of a suspension culture of the test organism (in the present case Alternaria mall) is added per Petri dish while the agar is still liquid, and the agar plates treated in this manner are subsequently incubated at about 22° C. To measure the inhibition of the fungus, the inhibition zone is measured after an incubation period of 3–4 days and recorded in mm.

TABLE 2
Fungicidal action against *Alternaria mali*

| Compounds according to Example | Inhibition zones in mm diameter at 1000 ppm of active substance and 20 μl per filter disk |
|---|---|
| 2.2 | 20 |
| 7.1 | 36 |
| 7.3 | 36 |
| 10.1 | 14 |
| 10.2 | 14 |
| 10.4 | 26 |
| 11.1 | 30 |
| 11.2 | 30 |
| 11.3 | 30 |

TABLE 2-continued

Fungicidal action against *Alternaria mali*

| Compounds according to Example | Inhibition zones in mm diameter at 1000 ppm of active substance and 20 μl per filter disk |
|---|---|
| 31.3 | 16 |
| untreated control | 0 |

EXAMPLE 3

Filter paper disks of diameter 6 mm are uniformly wetted with 20 μl portions of the active substances indicated in Table 3 and placed on an agar medium whose composition depends on the fungus species. Before this, 0.5 ml of a suspension culture of the test organism (in the present case Sclerotinia sclerotiorum, fragments of fungal hyphae) is added per Petri dish while the agar is still liquid, and the agar plates treated in this manner are subsequently incubated at about 22° C. To measure the inhibition of the fungus, the inhibition zone is measured after an incubation period of 3-4 days and recorded in mm.

TABLE 3

Fungicidal action against *Sclerotinia sclerotiorum*

| Compounds according to Example | Inhibition zones in mm diameter at 1000 ppm of active substance and 20 μl per filter disk |
|---|---|
| 2.2 | 14 |
| 7.1 | 40 |
| 7.3 | 50 |
| 10.2 | 14 |
| 10.4 | 20 |
| 30.1 | 12 |
| 31.2 | 20 |
| untreated control | 0 |

EXAMPLE 4

Barley plants in the 2-leaf stage were heavily inoculated with conidia of powdery mildew of barley (Erysiphe graminis hordei) and the plants were grown further in a greenhouse at 20° C. under relative atmospheric humidity of about 50%. One day after the inoculation, the plants were wetted uniformly with the compounds listed in Table 4 in the active ingredient concentrations given. After an incubation time of 7-9 days, the plants were examined for symptoms of powdery mildew of barley. The degree of effectiveness of the test substances was scored as a percentage relative to the untreated, infected control and can be seen from Table 4.

TABLE 4

| Compounds according to Example | Degree of effectiveness in % at mg of active substance/liter of spray liquor 500 |
|---|---|
| 9.17 | 100 |
| 2.49 | 100 |
| 7.8 | 100 |
| 7.12 | 90 |
| 8.2 | 90 |
| 8.5 | 100 |
| 7.14 | 100 |
| 7.15 | 100 |
| 7.16 | 100 |
| 2.8 | 90 |
| 2.11 | 100 |
| 101.1 | 100 |
| 6.9 | 90 |
| 102.11 | 100 |

TABLE 4-continued

| Compounds according to Example | Degree of effectiveness in % at mg of active substance/liter of spray liquor 500 |
|---|---|
| 102.21 | 100 |
| 102.16 | 100 |
| 102.17 | 100 |
| 102.33 | 100 |
| untreated, infected plants | 0 |

EXAMPLE 5

Field beans cv. "Harz Freya" or "Frank's Ackerperle", about 14 days old, were treated to runoff point with aqueous suspensions of the claimed compounds.

After the spray coating had dried on, the plants were inoculated with a spore suspension (1.5 mio spores/ml) of Botrytis cinerea. The plants were grown further in a controlled-environment chamber at 20°-22° C. and about 99% relative atmospheric humidity. Infection of the plants becomes apparent as black spots appear on the leaves and stalks. The tests are evaluated about 1 week after the inoculation.

The degree of effectiveness of the test substances was scored as a percentage in relation to the untreated, infected control and can be seen from Table 5.

TABLE 5

| Compounds according to Example | Degree of effectiveness in % at mg of active substance/liter of spray liquor 500 |
|---|---|
| 2.15 | 100 |
| 5.8 | 90 |
| 2.33 | 90 |
| 2.9 | 100 |
| 5.11 | 100 |
| 72.3 | 100 |
| 101.1 | 100 |
| 110.20 | 90 |
| 101.5 | 100 |
| 101.10 | 100 |
| 101.11 | 100 |
| 120.3 | 100 |
| 5.12 | 90 |
| 6.9 | 90 |
| 102.7 | 90 |
| 102.11 | 100 |
| 102.21 | 90 |
| 102.22 | 90 |
| 102.8 | 100 |
| 102.3 | 100 |
| 102.17 | 100 |
| 102.4 | 100 |
| 102.5 | 100 |
| 102.13 | 90 |
| 102.26 | 90 |
| 102.15 | 100 |
| 102.14 | 100 |
| 102.32 | 100 |
| 6.13 | 100 |
| 6.8 | 100 |
| 9.16 | 90 |
| 9.18 | 90 |
| 2.34 | 90 |
| 2.41 | 100 |
| 2.40 | 100 |
| 2.42 | 90 |
| 2.45 | 90 |
| 2.48 | 90 |
| 7.18 | 100 |
| 2.49 | 100 |
| 2.51 | 90 |
| 7.19 | 100 |
| 7.8 | 100 |

TABLE 5-continued

| Compounds according to Example | Degree of effectiveness in % at mg of active substance/liter of spray liquor 500 |
|---|---|
| 52.4 | 90 |
| 52.3 | 100 |
| 8.1 | 90 |
| 8.2 | 100 |
| 8.5 | 90 |
| 7.13 | 90 |
| 7.14 | 90 |
| 7.15 | 90 |
| 2.8 | 90 |
| 3.7 | 90 |
| 2.11 | 100 |
| 2.13 | 100 |
| 3.8 | 90 |
| 2.16 | 100 |
| 102.29 | 100 |
| 102.30 | 100 |
| 1.1 | 100 |
| 1.2 | 100 |
| 1.4 | 100 |
| 2.8 | 100 |
| 2.1 | 100 |
| 2.2 | 100 |
| 2.3 | 100 |
| 2.4 | 100 |
| 2.5 | 100 |
| 2.7 | 100 |
| 7.3 | 100 |
| 10.1 | 100 |
| 10.2 | 100 |
| 10.3 | 100 |
| 10.4 | 100 |
| 11.2 | 100 |
| 30.1 | 100 |
| 31.2 | 100 |
| 2.6 | 100 |
| untreated, infected plants | 0 |

EXAMPLE 6

Rice plants cv. "Ballila", about 5 weeks old, were presprayed with 0.05% strength gelatin solution and then treated with the claimed compounds in the concentrations given below. After the spray coating had dried on, the plants were inoculated uniformly with a spore suspension of Pyricularia oryzae and placed for 48 hours in a darkened controlled-environment chamber at a temperature of 25° C. and 100% relative atmospheric humidity. The rice plants were then grown further in a greenhouse at a temperature of 25° C. and 80% relative atmospheric humidity. The diseases were assessed after 5 days. The degree of effectiveness of the test substances were scored as a percentage relative to the untreated, infected control and can be seen from Table 6.

TABLE 6

| Compounds according to Example | Degree of effectiveness in % at mg of active substance/liter of spray liquor 500 |
|---|---|
| 9.17 | 100 |
| 2.34 | 100 |
| 2.41 | 100 |
| 2.43 | 100 |
| 2.45 | 100 |
| 2.46 | 100 |
| 2.48 | 100 |
| 2.47 | 100 |
| 2.49 | 100 |
| 7.18 | 100 |
| 2.51 | 90 |
| 7.20 | 90 |
| 7.8 | 100 |
| 7.7 | 90 |
| 7.10 | 90 |
| 7.11 | 100 |
| 7.12 | 100 |
| 8.2 | 100 |
| 8.5 | 100 |
| 7.13 | 100 |
| 7.14 | 100 |
| 7.15 | 100 |
| 7.16 | 100 |
| 2.19 | 100 |
| 3.6 | 90 |
| 2.11 | 100 |
| 2.21 | 100 |
| 3.4 | 90 |
| 2.14 | 90 |
| 3.8 | 100 |
| 2.33 | 90 |
| 2.9 | 100 |
| 120.1 | 90 |
| 120.6 | 90 |
| 6.9 | 100 |
| 102.11 | 100 |
| 102.21 | 100 |
| 102.16 | 100 |
| 102.22 | 100 |
| 102.17 | 100 |
| 102.23 | 100 |
| 102.18 | 100 |
| 102.13 | 90 |
| 102.32 | 100 |
| 102.29 | 100 |
| 1.1 | 100 |
| 1.2 | 100 |
| 2.1 | 100 |
| 2.2 | 100 |
| 7.1 | 100 |
| 7.3 | 100 |
| untreated, infected plants | 0 |

EXAMPLE 7

Wheat cv. "Jubilar" in the 2-leaf stage was treated to runoff point with aqueous suspensions of the claimed compounds.

After the spray coating had dried on, the plants were inoculated with aqueous spore suspensions of Puccinia recondita. The dripping wet plants were placed in a controlled-environment chamber at 20° C. and about 100% relative atmospheric humidity for about 16 hours. The infected plants were subsequently grown further in a greenhouse at a temperature of 22°-25° C. and 50-70% relative atmospheric humidity.

After an incubation time of about 2 weeks, the fungus sporulates on the entire leaf surface of the untreated control plants, so that the test plants can be assessed for disease. The degree of effectiveness of the test is substances was scored as a percentage in relation to the untreated, infected control and can be seen from Table 7.

TABLE 7

| Compounds according to Example | Degree of effectiveness in % at mg of active substance/liter of spray liquor 500 |
|---|---|
| 9.16 | 90 |
| 9.17 | 100 |

TABLE 7-continued

| Compounds according to Example | Degree of effectiveness in % at mg of active substance/liter of spray liquor 500 |
|---|---|
| 9.18 | 100 |
| 2.45 | 90 |
| 2.49 | 90 |
| 7.8 | 100 |
| 7.11 | 90 |
| 7.12 | 100 |
| 8.5 | 100 |
| 7.14 | 100 |
| 7.15 | 100 |
| 7.16 | 100 |
| 2.8 | 100 |
| 2.19 | 100 |
| 3.6 | 100 |
| 2.11 | 100 |
| 2.21 | 90 |
| 2.14 | 90 |
| 2.16 | 90 |
| 5.8 | 100 |
| 2.9 | 100 |
| 3.5 | 90 |
| 120.5 | 90 |
| 6.9 | 90 |
| 102.11 | 100 |
| 102.17 | 100 |
| 102.10 | 100 |
| 102.33 | 100 |
| 1.1 | 100 |
| 1.2 | 100 |
| 2.7 | 100 |
| 2.1 | 100 |
| 2.2 | 100 |
| 7.1 | 100 |
| 31.3 | 100 |
| 7.3 | 100 |
| untreated, infected plants | 0 |

EXAMPLE 8

About 6 weeks after sowing, vine seedlings cv. "Riesling/Ehrenfelder" were treated to runoff point with aqueous suspension of the claimed compound.

After the spray coating had dried on, the plants were inoculated with a zoosporangia suspension of Plasmopara viticola, and the dripping wet plants were placed in a controlled-environment chamber at 23° C. at 80–90% relative atmospheric humidity.

After an incubation time of 7 days, the plants were placed in the controlled-environment chamber overnight in order to encourage sporulation of the fungus. The plants were then assessed for disease. The degree of effectiveness of the test substances was scored as a percentage relative to the untreated, infected control and can be seen from Table 8.

TABLE 8

| Compounds according to Example | Degree of effectiveness in % at mg of active substance/liter of spray liquor 500 |
|---|---|
| 2.51 | 90 |
| 52.5 | 100 |
| 7.14 | 90 |
| 2.8 | 100 |
| 101.1 | 90 |
| 101.11 | 90 |
| 120.5 | 90 |
| 102.11 | 90 |
| 102.27 | 100 |
| 102.5 | 100 |
| 102.31 | 100 |
| 102.10 | 90 |

TABLE 8-continued

| Compounds according to Example | Degree of effectiveness in % at mg of active substance/liter of spray liquor 500 |
|---|---|
| 102.20 | 90 |
| 2.7 | 100 |
| untreated, infected plants | 0 |

EXAMPLE 9

Wheat plants cv. liubilar, in the 2-leaf stage were treated to runoff point with aqueous suspensions of the preparations given in Table 9.

After the spray coating had dried on, the plants were inoculated with an aqueous pyknospore suspension of Leptosphaeria nodorum and incubated for several hours in a controlled-environment chamber at 100% relative atmospheric humidity. The plants were grown further in a greenhouse at about 90% relative atmospheric humidity until the symptoms became apparent.

The degree of effectiveness is expressed as a percentage relative to the untreated, infected control and can be seen from Table 9.

TABLE 9

| Compounds according to Example | Degree of effectiveness in % at mg of active substance/liter of spray liquor 500 |
|---|---|
| 6.11 | 100 |
| 6.12 | 100 |
| 6.13 | 100 |
| 6.8 | 100 |
| 9.17 | 100 |
| 9.18 | 100 |
| 2.34 | 100 |
| 2.40 | 100 |
| 2.41 | 100 |
| 2.42 | 100 |
| 2.43 | 100 |
| 2.45 | 100 |
| 2.46 | 100 |
| 2.47 | 100 |
| 2.48 | 100 |
| 2.50 | 100 |
| 2.49 | 100 |
| 7.18 | 100 |
| 2.51 | 100 |
| 7.19 | 100 |
| 7.20 | 100 |
| 7.8 | 100 |
| 7.10 | 100 |
| 7.7 | 90 |
| 20.8 | 100 |
| 52.4 | 90 |
| 51.1 | 90 |
| 52.5 | 90 |
| 51.3 | 90 |
| 53.1 | 100 |
| 52.1 | 100 |
| 53.2 | 100 |
| 52.2 | 100 |
| 52.3 | 100 |
| 53.4 | 100 |
| 7.12 | 100 |
| 8.1 | 100 |
| 8.2 | 100 |
| 8.3 | 100 |
| 8.4 | 100 |
| 8.5 | 100 |
| 7.13 | 100 |
| 7.15 | 100 |
| 7.14 | 100 |
| 7.16 | 100 |
| 8.6 | 90 |

TABLE 9-continued

| Compounds according to Example | Degree of effectiveness in % at mg of active substance/liter of spray liquor 500 |
|---|---|
| 2.8 | 100 |
| 2.19 | 100 |
| 3.6 | 100 |
| 2.11 | 100 |
| 2.14 | 100 |
| 3.7 | 100 |
| 2.13 | 100 |
| 2.21 | 100 |
| 3.4 | 100 |
| 2.14 | 100 |
| 2.16 | 100 |
| 3.8 | 100 |
| 2.17 | 100 |
| 2.15 | 100 |
| 2.18 | 100 |
| 2.33 | 100 |
| 5.8 | 100 |
| 2.9 | 100 |
| 3.5 | 100 |
| 5.11 | 100 |
| 72.3 | 100 |
| 110.15 | 100 |
| 101.3 | 100 |
| 101.9 | 100 |
| 120.2 | 90 |
| 120.3 | 90 |
| 101.1 | 90 |
| 120.6 | 100 |
| 5.12 | 100 |
| 6.9 | 100 |
| 6.10 | 100 |
| 120.7 | 100 |
| 102.11 | 100 |
| 102.21 | 100 |
| 102.8 | 100 |
| 102.16 | 100 |
| 102.22 | 100 |
| 102.17 | 100 |
| 102.23 | 100 |
| 102.4 | 90 |
| 102.18 | 100 |
| 102.3 | 100 |
| 102.19 | 100 |
| 102.5 | 90 |
| 102.6 | 100 |
| 102.31 | 100 |
| 102.9 | 100 |
| 102.14 | 100 |
| 102.32 | 100 |
| 102.33 | 100 |
| 102.29 | 100 |
| 102.30 | 100 |
| 1.1 | 100 |
| 1.2 | 100 |
| 1.3 | 100 |
| 1.4 | 100 |
| 2.7 | 100 |
| 2.1 | 100 |
| 2.38 | 100 |
| 2.2 | 100 |
| 7.1 | 100 |
| 7.3 | 100 |
| 10.3 | 100 |
| 10.2 | 100 |
| 10.4 | 100 |
| 11.1 | 100 |
| 11.2 | 100 |
| 11.3 | 100 |
| 31.2 | 100 |
| untreated, infected plants | 0 |

EXAMPLE 10

Barley plants cv. "Igri" in the 2-leaf stage were treated to runoff point with an aqueous suspension of the claimed compounds.

After the spray coating had dried on, the plants were inoculated with aqueous spore suspensions of Pyrenophora teres and incubated for 16 hours in a controlled-environment chamber at 100% relative atmospheric humidity. The infected plants were subsequently grown further in a greenhouse at 25° C. and 80% relative atmospheric humidity.

The disease was assessed about 1 week after the inoculation. The degree of effectiveness of the test substances was scored as a percentage relative to the untreated, infected control and can be seen from Table 10.

TABLE 10

| Compounds according to Example | Degree of effectiveness in % at mg of active substance/liter of spray liquor 500 |
|---|---|
| 6.11 | 90 |
| 6.12 | 100 |
| 6.13 | 100 |
| 9.17 | 90 |
| 9.18 | 100 |
| 2.34 | 100 |
| 2.40 | 100 |
| 2.41 | 90 |
| 2.42 | 90 |
| 2.43 | 90 |
| 2.46 | 100 |
| 2.48 | 100 |
| 2.49 | 100 |
| 7.18 | 100 |
| 2.51 | 100 |
| 7.19 | 100 |
| 7.11 | 90 |
| 52.5 | 100 |
| 51.3 | 100 |
| 7.12 | 90 |
| 8.1 | 90 |
| 8.2 | 100 |
| 8.3 | 90 |
| 7.13 | 100 |
| 7.15 | 90 |
| 7.14 | 100 |
| 7.16 | 90 |
| 2.8 | 100 |
| 2.19 | 100 |
| 3.6 | 90 |
| 2.11 | 90 |
| 2.14 | 100 |
| 2.13 | 100 |
| 2.21 | 100 |
| 3.4 | 100 |
| 2.14 | 100 |
| 3.8 | 100 |
| 2.16 | 90 |
| 2.15 | 100 |
| 2.18 | 100 |
| 2.33 | 100 |
| 5.11 | 100 |
| 2.9 | 90 |
| 101.1 | 100 |
| 101.3 | 100 |
| 101.5 | 100 |
| 101.4 | 90 |
| 120.2 | 100 |
| 120.3 | 100 |
| 120.4 | 100 |
| 6.10 | 100 |
| 6.14 | 100 |
| 5.12 | 90 |
| 102.21 | 100 |
| 102.22 | 100 |
| 102.3 | 100 |

TABLE 10-continued

| Compounds according to Example | Degree of effectiveness in % at mg of active substance/liter of spray liquor 500 |
|---|---|
| 102.23 | 100 |
| 120.8 | 90 |
| 102.19 | 100 |
| 102.27 | 100 |
| 102.6 | 90 |
| 102.15 | 100 |
| 102.31 | 100 |
| 102.9 | 100 |
| 102.32 | 100 |
| 102.29 | 100 |
| 102.30 | 100 |
| 2.7 | 100 |
| 7.1 | 100 |
| 10.3 | 100 |
| 10.2 | 100 |
| 11.2 | 100 |
| 11.3 | 100 |
| untreated, infected plants | 0 |

EXAMPLE 11

Tomato plants cv. "Rheinlands Ruhm" in the 3-4 leaf stage were uniformly wetted to runoff point with aqueous suspensions of the claimed compounds.

After the coating had dried on, the plants were inoculated with a zoosporangia suspension of Phytophthora infestans and kept in a controlled-environment chamber with optimum infection conditions for 2 days. The plants were then grown further in the greenhouse until the symptoms became apparent.

The plants were scored for disease about 1 week after the inoculation. The degree of effectiveness of the test substances was scored as a percentage relative to the untreated, infected control and can be seen from Table 11.

TABLE 11

| Compounds according to Example | Degree of effectiveness in % at mg of active substance/liter of spray liquor 500 |
|---|---|
| 2.34 | 90 |
| 2.40 | 100 |
| 2.41 | 100 |
| 2.49 | 100 |
| 7.18 | 100 |
| 7.8 | 90 |
| 7.11 | 90 |
| 8.1 | 100 |
| 7.12 | 90 |
| 8.2 | 100 |
| 2.19 | 90 |
| 2.13 | 100 |
| 2.21 | 100 |
| 2.16 | 90 |
| 2.18 | 90 |
| 2.9 | 100 |
| 101.1 | 90 |
| 101.5 | 90 |
| 102.5 | 90 |
| 102.33 | 90 |
| 10.3 | 100 |
| 10.2 | 100 |
| 10.4 | 100 |
| untreated, infected plants | 0 |

We claim:
1. A compound of the formula I

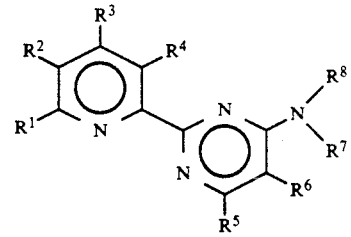

wherein $R^1$ is $(C_2-C_6)$alkyl, $(C_1-C_4)$alkoxy-$(C_1-C_4)$alkyl, $(C_1-C_4)$alkylthio-$(C_1-C_4)$alkyl, $(C_2-C_6)$alkenyl, $(C_2-C_6)$alkynyl, $(C_3-C_7)$cycloalkyl and $C_3-C_7$cycloalkyl-$(C_1-C_4)$alkyl, where the last two radicals can be up to trisubstituted in the cycloalkyl moiety by $(C_1-C_4)$alkyl, or is a group $R^7R^8N$-$(C_1-C_4)$-alkyl, phenyl, phenoxy-$(C_1-C_4)$alkyl, phenylmercapto-$(C_1-C_4)$-alkyl, phenyl-$(C_1-C_4)$alkyl and phenoxyphenoxy-$(C_1-C_4)$alkyl, where the last five radicals can be up to trisubstituted in the phenyl moiety by halogen, nitro, cyano, $(C_1-C_4)$alkyl, $(C_1-C_4)$alkoxy, $(C_1-C_4)$-alkylthio, $(C_1-C_4)$haloalkyl or $(C_1-C_4)$haloalkoxy, $R^2$, $R^3$ and $R^4$ independently of one another are hydrogen, $(C_1-C_6)$alkyl or phenyl, where the phenyl radical can be up to trisubstituted by halogen, nitro, cyano, $(C_1-C_4)$alkyl, $(C_1-C_4)$alkylthio, $(C_1-C_4)$haloalkyl or $(C_1-C_4)$haloalkoxy, $R^5$ is hydrogen, $(C_1-C_6)$alkyl, $(C_3-C_7)$cycloalkyl or $(C_3-C_7)$-cycloalkyl-$(C_1-C_4)$alkyl, where the last two radicals can be up to trisubstituted in the cycloalkyl moiety by $(C_1-C_4)$alkyl, or is $(C_1-C_4)$haloalkyl, $(C_1-C_4)$alkoxy, $(C_1-C_4)$alkylthio, $(C_1-C_4)$alkoxy-$(C_1-C_4)$alkyl, a group $R^7R^8N$-, $(C_1-C_4)$alkylthio-$(C_1-C_4)$alkyl, a group $R^7R^8N$-$(C_1-C_4)$alkyl, $(C_2-C_6)$alkenyl, $(C_2-C_6)$alkynyl, phenoxy, phenyl$(C_1-C_4)$alkyl, phenoxy-$(C_1-C_4)$alkyl, phenyl-mercapto-$(C_1-C_4)$alkyl, phenylmercapto, phenyl-$(C_1-C_4)$alkoxy or phenyl-$(C_1-C_4)$alkylthio, where the last seven radicals can be up to trisubstituted in the phenyl moiety by halogen, nitro, cyano, $(C_1-C_4)$alkyl, $(C_1-C_4)$alkoxy, $(C_1-C_4)$halo-alkyl or $(C_1-C_4)$haloalkoxy;

$R^6$ is hydrogen, $(C_1-C_4)$alkyl, $(C_1-C_4)$alkoxy, $(C_2-C_5)$alkenyloxy, $(C_2-C_6)$alkynyloxy, $(C_1-C_4)$alkylthio, halogen or phenyl, where the phenyl radical can be up to trisubstituted by halogen, nitro, cyano, $(C_1-C_4)$alkyl, $(C_1-C_4)$alkoxy, $(C_1-C_4)$alkylthio, $(C_1-C_4)$haloalkyl or $(C_1-C_4)$haloalkoxy, or $R^5$ and $R^6$ together form a polymethylene chain of the formula $-(CH_2)_m-$ with m being 3-4 and $R^7$ and $R^8$ independently of one another are hydrogen, $(C_1-C_6)$alkyl, $(C_1-C_4)$alkoxy-$(C_1-C_6)$alkyl, hydroxy-$(C_1-C_6)$alkyl, $(C_1-C_4)$alkylthio-$(C_1-C_6)$alkyl, $R^9R^{10}N$-$(C_1-C_6)$alkyl, $(C_3-C_6)$alkenyl, $(C_3-C_6)$alkynyl, $(C_3-C_7)$cycloalkyl or $(C_3-C_7)$cycloalkyl-$(C_1-C_4)$alkyl, where the last two radicals can be up to trisubstituted in the cycloalkyl moiety by $(C_1-C_4)$alkyl; or are formyl, phenyl or phenyl-$(C_1-C_4)$alkyl, where the last two radicals can be up to trisubstituted in the phenyl moiety by halogen, nitro, cyano, $(C_1-C_4)$alkyl, $(C_1-C_4)$alkoxy, $(C_1-C_4)$alkylthio, $(C_1-C_4)$haloalkyl or $(C_1-C_4)$haloalkoxy;

or the two radicals $R^7$ and $R^8$ together with the nitrogen atom to which they are bonded stand for a heterocycle selected from the group consisting of piperidine, pyrrolidine, morpholine, pyrrole, piperazine and hexahydroazepine, which heterocycle is unsubstituted or up to tetrasubstituted by $(C_1-C_4)$alkyl);

$R^9$ and $R^{10}$ independently of one another are hydrogen, $(C_1-C_6)$alkyl, $(C_3-C_6)$alkenyl, $(C_3-C_6)$alkynyl, $(C_3-C_7)$-cycloalkyl or $(C_3-C_7)$cycloalkyl-$(C_1-C_4)$alkyl, where the last two radicals can be up to trisubstituted in the cycloalkyl moiety by $(C_1-C_4)$alkyl; or are formyl, phenyl, phenyl$(C_1-C_4)$alkyl, where the last two radicals can be up to trisubstituted in the phenyl moiety by halogen, nitro, cyano, $(C_1-C_4)$-alkyl, $(C_1-C_4)$alkoxy, $(C_1-C_4)$alkylthio, $(C_1-C_4)$haloalkyl or $(C_1-C_4)$haloalkoxy;

or the two radicals $R^9$ and $R^{10}$ together with the nitrogen atom to which they are bonded strand for pyrrolidine and the acid addition salts thereof.

2. The compound of the formula I of claim 1, where $R^1$ is $(C_2-C_6)$alkyl, phenyl, phenyl-$(C_1-C_2)$alkyl, phenoxyphenoxy$(C_1-C_2)$alkyl or phenoxy-$(C_1-C_2)$alkyl, where the last four radicals can be up to trisubstituted in the phenyl moiety by halogen or $(C_1-C_4)$alkyl; or is $(C_1-C_3)$alkoxy-$(C_1-C_2)$alkyl, $R^2$ and $R^3$ independently of one another are hydrogen, $(C_1-C_3)$alkyl or phenyl, where the phenyl radical can be up to trisubstituted by halogen or $(C_1-C_4)$alkyl, $R^4$ is hydrogen, $R^5$ is hydrogen, $(C_1-C_6)$alkyl, $(C_3-C_6)$cycloalkyl, $(C_5-C_6)$cycloalkyl-$(C_1-C_3)$alkyl, or phenyl$(C_1-C_2)$alkyl, where the last radical can be unsubstituted or up to trisubstituted in the phenyl moiety by halogen, $(C_1-C_4)$alkyl or $(C_1-C_4)$alkoxy, $R^6$ is hydrogen, $(C_1-C_4)$alkyl, halogen, phenyl or $(C_1-C_3)$alkoxy, or $R^5$ and $R^6$ together form a polymethylene chain of the formula $-(CH_2)_m-$ with m being 3-4, and $R^7$ and $R^8$ independently of one another are hydrogen, $(C_1-C_6)$alkyl, $(C_1-C_4)$alkoxy-$(C_1-C_6)$alkyl, hydroxy-$(C_1-C_6)$alkyl, $(C_1-C_4)$alkylthio-$(C_1-C_6)$alkyl, $R^9R^{10}N$-$(C_1-C_6)$alkyl, $(C_3-C_4)$alkenyl, $(C_3-C_4)$alkynyl, $(C_3-C_6)$cycloalkyl or $(C_3-C_6)$cycloalkyl-$(C_1-C_3)$alkyl, where the last two radicals can be up to disubstituted in the cycloalkyl moiety by $(C_1-C_2)$alkyl; or are formyl, phenyl or phenyl-$(C_1-C_2)$alkyl, where the last two radicals can be up to disubstituted in the phenyl moiety by halogen, $(C_1-C_3)$alkyl, $(C_1-C_3)$alkoxy, trifluoromethyl or trichloromethyl; or the two radicals $R^7$ and $R^8$ together with the nitrogen atom to which they are bonded stand for a heterocycle selected from the group consisting of piperidine, pyrrolidine, morpholine, pyrrole, piperazine and hexahydroazepine, which heterocycle is unsubstituted or up to tetrasubstituted by $(C_1-C_4)$alkyl;

$R^9$ and $R^{10}$ independently of one another are hydrogen, $(C_1-C_6)$alkyl, $(C_3-C_6)$alkenyl, $(C_3-C_6)$alkynyl, $(C_3-C_7)$cycloalkyl or $(C_3-C_7)$cycloalkyl-$(C_1-C_4)$alkyl, where the last two radicals can be up to trisubstituted in the cycloalkyl moiety by $(C_1-C_4)$alkyl; or are formyl, phenyl, phenyl$(C_1-C_4)$alkyl, where the last two radicals can be up to trisubstituted in the phenyl moiety by halogen, nitro, cyano, $(C_1-C_4)$alkyl, $(C_1-C_4)$alkoxy, $(C_1-C_4)$alkylthio, $(C_1-C_4)$haloalkyl or $(C_1-C_4)$haloalkoxy; or the two radicals $R^9$ $R^{10}$ together with the nitrogen atom to which they are bonded stand for pyrrolidine and the acid addition salts thereof.

3. A fungicidal composition, containing an effective amount of a compound of the formula I

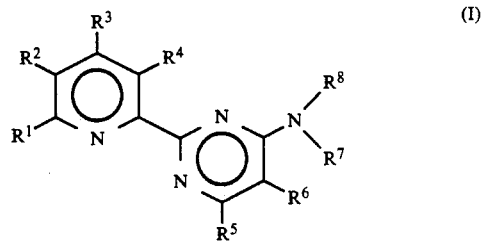

where
$R^1$ is $(C_2-C_6)$alkyl, $(C_1-C_4)$alkoxy-$(C_1-C_4)$alkyl, $(C_1-C_4)$alkylthio-$(C_1-C_4)$alkyl, $(C_2-C_6)$alkenyl, $(C_2-C_6)$alkynyl, $(C_3-C_7)$cycloalkyl and $(C_3-C_7)$cycloalkyl-$(C_1-C_4)$alkyl, where the last two radicals can be up to trisubstituted in the cycloalkyl moiety by $(C_1-C_4)$alkyl, or is a group $R^7R^8N$-$(C_1-C_4)$alkyl, phenyl, phenoxy-$(C_1-C_4)$alkyl, phenylmercapto-$(C_1-C_4)$alkyl, phenyl-$(C_1-C_4)$alkyl and phenoxyphenoxy-$(C_1-C_4)$alkyl, where the last five radicals can be up to trisubstituted in the phenyl moiety by halogen, nitro, cyano, $(C_1-C_4)$alkyl, $(C_1-C_4)$alkoxy, $(C_1-C_4)$alkylthio, $(C_1-C_4)$haloalkyl or $(C_1-C_4)$haloalkoxy, $R^2$, $R^3$ and $R^4$ independently of one another are hydrogen, $(C_1-C_6)$alkyl or phenyl, where the phenyl radical can be up to trisubstituted by halogen, nitro, cyano, $(C_1-C_4)$alkyl, $(C_1-C_4)$alkoxy, $(C_1-C_4)$alkylthio, $(C_1-C_4)$haloakyl or $(C_1-C_4)$haloalkoxy, $R^5$ is hydrogen, $(C_1-C_6)$alkyl, $(C_3-C_7)$cycloalkyl or $(C_3-C_7)$cycloalkyl-$C_1-C_4)$alkyl, where the last two radicals can be up to trisubstituted in the cycloalkyl moiety by $(C_1-C_4)$alkyl, or is $(C_1-C_4)$haloalkyl, $(C_1-C_4)$alkoxy, $(C_1-C_4)$alkylthio, $(C_1-C_4)$alkoxy-$(C_1-C_4)$alkyl, a group $R^7R^8N$-, $(C_1-C_4)$alkylthio-$(C_1-C_4)$alkyl, a group $R^7R^8N$-$(C_1-C_4)$alkyl, halogen, $(C_2-C_6)$alkenyl, $(C_2-C_6)$alkynyl, phenoxy, phenyl$(C_1-C_4)$alkyl, phenoxy-$(C_1-C_4)$alkyl, phenyl-mercapto-$(C_1-C_4)$alkyl, phenylmercapto, phenyl-$(C_1-C_4)$alkoxy or phenyl$(C_1-C_4)$alkylthio, where the last eight radicals can be up to trisubstituted in the phenyl moiety by halogen, nitro, cyano, $(C_1-C_4)$alkyl, $(C_1-C_4)$alkoxy, $(C_1-C_4)$alkylthio, $(C_1-C_4)$haloalkyl or $(C_1-C_4)$haloalkoxy;

$R^6$ is hydrogen, $(C_1-C_4)$alkyl, $(C_1-C_4)$alkoxy, $(C_2-C_5)$alkenyloxy, $(C_2-C_6)$alkynyloxy, $(C_1-C_4)$alkylthio, halogen or phenyl, where the phenyl radical can be up to trisubstituted by halogen, nitro, cyano, $(C_1-C_4)$alkyl, $(C_1-C_4)$alkoxy, $(C_1-C_4)$alkylthio, $(C_1-C_4)$haloalkyl or $(C_1-C_4)$haloalkoxy, or $R^5$ $R^6$ together form a polymethylene chain of the formula $-(CH_2)_m-$ with m being 3-4 and $R^7$ and $R^8$ independently of one another are hydrogen, $(C_1-C_6)$alkyl, $(C_1-C_4)$alkoxy-$(C_1-C_6)$alkyl, hydroxy-$(C_1-C_6)$alkyl, $(C_1-C_4)$alkylthio-$(C_1-C_6)$alkyl, $(R^9R^{10}N$-$C_1-C_6)$alkyl, $(C_3-C_6)$alkenyl, $(C_3-C_6)$alkynyl, $(C_3-C_7)$cycloalkyl or $(C_3-C_7)$cycloalkyl-$(C_1-C_4)$alkyl, where the last two radicals can be up to trisubstituted in the cycloalkyl moiety by $(C_1-C_4)$alkyl; or are formyl, phenyl or phenyl-$(C_1-C_4)$alkyl, where the last two radicals can be up to trisubstituted in the phenyl moiety by halogen, nitro, cyano, $(C_1-C_4)$alkyl, $(C_1-C_4)$alkoxy, $(C_1-C_4)$alkylthio, $(C_1-C_4)$haloalkyl or $(C_1-C_4)$haloalkoxy; or the two radicals $R^7$ and $R^8$ together with the nitrogen atom to which they are bonded stand for a heterocycle selected from the group consisting of piperdine, pyrrolidine, morpholine, pyrrole, piperazine and hexahydroazepine, which heterocycle is unsubstituted or up to tetrasubstituted by $(C_1-C_4$alkyl);

$R^9$ and $R^{10}$ independently of one another are hydrogen, $(C_1-C_6)$alkyl, $(C_3-C_6)$alkenyl, $(C_3-C_6)$alkynyl, $(C_3-C_7)$cycloalkyl or $(C_3-C_7)$cycloalkyl-$(C_1-C_4)$alkyl, where the last two radicals can be up to trisubstituted in the cycloalkyl moiety by $(C_1-C_4)$alkyl; or are formyl, phenyl, phenyl$(C_1-C_4)$alkyl, where the last two radicals can be up to trisubstituted in the phenyl moiety by halogen, nitro, cyano, $(C_1-C_4)$alkyl, $(C_1-C_4)$alkoxy, $(C_1-C_4)$alkylthio, $(C_1-C_4)$-haloalkyl or $(C_1-C_4)$haloalkoxy; or the two radicals $R^9$ and $R^{10}$ together with the nitrogen atom to which they are bonded stand for pyrrolidine and the acid addition salts thereof, and formulation auxiliaries.

4. A fungicidal composition, containing an effective amount of a compound of the formula I of claim 1, where $R^1$ is $(C_2-C_6)$alkyl, phenyl, phenyl-$(C_1-C_2)$alkyl, phenoxyphenoxy$(C_1-C_2)$alkyl or phenoxy-$(C_1-C_2)$alkyl, where the last four radicals can be up to trisubstituted in the phenyl moiety by halogen or $(C_1-C_4)$alkyl; or is $(C_1-C_3)$alkoxy-$(C_1-C_2)$alkyl, $R^2$ and $R^3$ independently of one another are hydrogen, $(C_1-C_3)$alkyl or phenyl, where the phenyl radical can be up to trisubstituted by halogen or $(C_1-C_4)$alkyl, $R^4$ is hydrogen, $R^5$ is hydrogen, $(C_1-C_6)$alkyl, $(C_3-C_6)$cycloalkyl, $(C_5-C_6)$cycloalkyl-$(C_1-C_3)$alkyl, halogen, or phenyl-$(C_1-C_2)$alkyl, where the last two radicals can be unsubstituted or up to trisubstituted in the phenyl moiety by halogen, $(C_1-C_4)$alkyl or $(C_1-C_4)$alkoxy, $R^6$ is hydrogen, $(C_1-C_4)$alkyl, halogen, phenyl or $(C_1-C_3)$alkoxy, or $R^5$ and $R^6$ together form a polymethylene chain of the formula $-(CH_2)_m-$ with m being 3-4, and $R^7$ and $R^8$ independently of one another are hydrogen, $(C_1-C_6)$alkyl, $(C_1-C_4)$alkoxy-$(C_1-C_6)$alkyl, hydroxy-$(C_1-C_6)$alkyl, $(C_1-C_4)$alkylthio-$(C_1-C_6)$alkyl, $R^9R^{10}N$-$(C_1-C_6)$alkyl, $(C_3-C_4)$alkenyl, $(C_3-C_4)$alkynyl, $(C_3-C_6)$cycloalkyl or $(C_3-C_6)$cycloalkyl-$(C_1-C_3)$alkyl, where the last two radicals can be up to disubstituted in the cycloalkyl moiety by $(C_1-C_2)$alkyl; or are formyl, phenyl or phenyl-$(C_1-C_2)$alkyl, where the last two radicals can be up to disubstituted in the phenyl moiety by halogen, $(C_1-C_3)$alkyl, $(C_1-C_3)$-alkoxy, trifluoromethyl or trichloromethyl; or the two radicals $R^7$ and $R^8$ together with the nitrogen atom to which they are bonded stand for a heterocycle selected from the group consisting of piperidine, pyrrolidine, morpholine, pyrrole, piperazine and hexahydroazepine, which heterocycle is unsubstituted or up to tetrasubstituted by $(C_1-C_4$-alkyl);

$R^9$ and $R^{10}$ and independently of one another are hydrogen, $(C_1-C_6)$alkyl, $(C_3-C_6)$alkenyl, $(C_3-C_6)$alkynyl, $(C_3-C_7)$cycloalkyl, or $(C_3-C_7)$cycloalkyl-$(C_1-C_4)$alkyl, where the last two radicals can be up to trisubstituted in the cycloalkyl moiety by $(C_1-C_4)$alkyl; or are formyl, phenyl, phenyl$(C_1-C_4)$alkyl, where the last two radicals can be up to trisubstituted in the phenyl moiety by halogen, nitro, cyano, $(C_1-C_4)$-alkyl, $(C_1-C_4)$alkoxy, $(C_1-C_4)$alkylthio, $(C_1-C_4)$-haloalkyl or $(C_1-C_4)$haloalkoxy; or the two radicals $R^9$ and $R^{10}$ together with the nitrogen atom to which they are bonded stand for pyrrolidine and the acid addition salts thereof, and formulation auxiliaries.

5. The fungicidal composition as claimed in claim 3 which contains 1 to 95% by weight of a compound of the formula I and 5 to 99.9% by weight of common formulation auxiliaries.

6. The fungicidal composition as claimed in claim 4 which contains 1 to 95% by weight of a compound of the formula I and 5 to 99.9% by weight of common formulation auxiliaries.

7. A method of controlling harmful fungi, which comprises applying an effective amount of a compound of the formula I according to claim 3 to the plants, areas or substrates which are diseased with the fungi.

8. A method of controlling harmful fungi, which comprises applying an effective amount of a compound of the formula I according to claim 4 to the plants, areas or substrates which are diseased with the fungi.

* * * * *